United States Patent
Franco

(10) Patent No.: US 7,153,823 B2
(45) Date of Patent: *Dec. 26, 2006

(54) METHODS OF USE OF FIBROBLAST GROWTH FACTOR, VASCULAR ENDOTHELIAL GROWTH FACTOR AND RELATED PROTEINS IN THE TREATMENT OF ACUTE AND CHRONIC HEART DISEASE

(76) Inventor: Wayne P. Franco, 500 Cold Spring Rd., No. E217, Rocky Hill, CT (US) 06067

( * ) Notice: Subject to any disclaimer, the term of this patent is extended or adjusted under 35 U.S.C. 154(b) by 0 days.

This patent is subject to a terminal disclaimer.

(21) Appl. No.: 10/730,831

(22) Filed: Dec. 9, 2003

(65) Prior Publication Data

US 2004/0116349 A1    Jun. 17, 2004

Related U.S. Application Data

(62) Division of application No. 09/828,330, filed on Apr. 6, 2001, now Pat. No. 6,759,386.

(60) Provisional application No. 60/195,624, filed on Apr. 6, 2000.

(51) Int. Cl.
*A61K 38/18*     (2006.01)
*C07K 14/475*   (2006.01)
*C07K 14/50*     (2006.01)

(52) U.S. Cl. ............... 514/2; 514/8; 514/12; 530/300; 530/350

(58) Field of Classification Search ............ 424/9.1; 514/2, 8, 12, 14; 530/300, 324, 399, 350
See application file for complete search history.

(56) References Cited

U.S. PATENT DOCUMENTS

| | | | |
|---|---|---|---|
| 4,296,100 A | 10/1981 | Franco | 424/108 |
| 4,409,237 A | 10/1983 | Cairns et al. | 424/283 |
| 5,006,343 A | 4/1991 | Benson et al. | 424/450 |
| 5,254,330 A | 10/1993 | Ganderton et al. | 424/46 |
| 5,915,378 A | 6/1999 | Lloyd et al. | 128/200.22 |
| 5,925,012 A | 7/1999 | Murphy-Chutorian et al. | 604/30 |
| 5,932,540 A * | 8/1999 | Hu et al. | 514/2 |
| 6,239,172 B1 * | 5/2001 | Kaesemeyer | 514/460 |
| 6,436,902 B1 | 8/2002 | Bäckström et al. | 514/12 |
| 6,475,796 B1 * | 11/2002 | Pollitt et al. | 435/455 |
| 6,620,784 B1 * | 9/2003 | Ferrara et al. | 514/12 |
| 6,737,404 B1 * | 5/2004 | Springer et al. | 514/12 |

FOREIGN PATENT DOCUMENTS

| | | | |
|---|---|---|---|
| WO | WO 98/49300 | 11/1998 | 15/12 |
| WO | WO 00/40086 | 7/2000 | 43/16 |
| WO | WO 200156593 A2 * | 8/2001 | |

OTHER PUBLICATIONS

Bikfalvi et al. (1997) "Biological Roles of Fibroblast Growth Factor-2." Endocrine Reviews 18(1): 26-45.*

* cited by examiner

*Primary Examiner*—David S Romeo
*Assistant Examiner*—Daniel C Gamett
(74) *Attorney, Agent, or Firm*—Ernest D. Buff & Associates,LLC; Ernest D. Buff; Theodore J. Pierson

(57) ABSTRACT

Disclosed herein is a rational, multi-tier approach to the administration of growth factor proteins in the treatment of heart disease. Also disclosed is a method to evaluate the effectiveness of the administration of growth factor proteins comprising the clinical assay of CPK-MB levels in a patient undergoing treatment with growth factor proteins. In addition, there is disclosed a method for treatment of heart disease comprising administration of a therapeutically effective amount of a growth factor protein by oral inhalation therapy.

8 Claims, 4 Drawing Sheets

FIG.1

Figure 2:
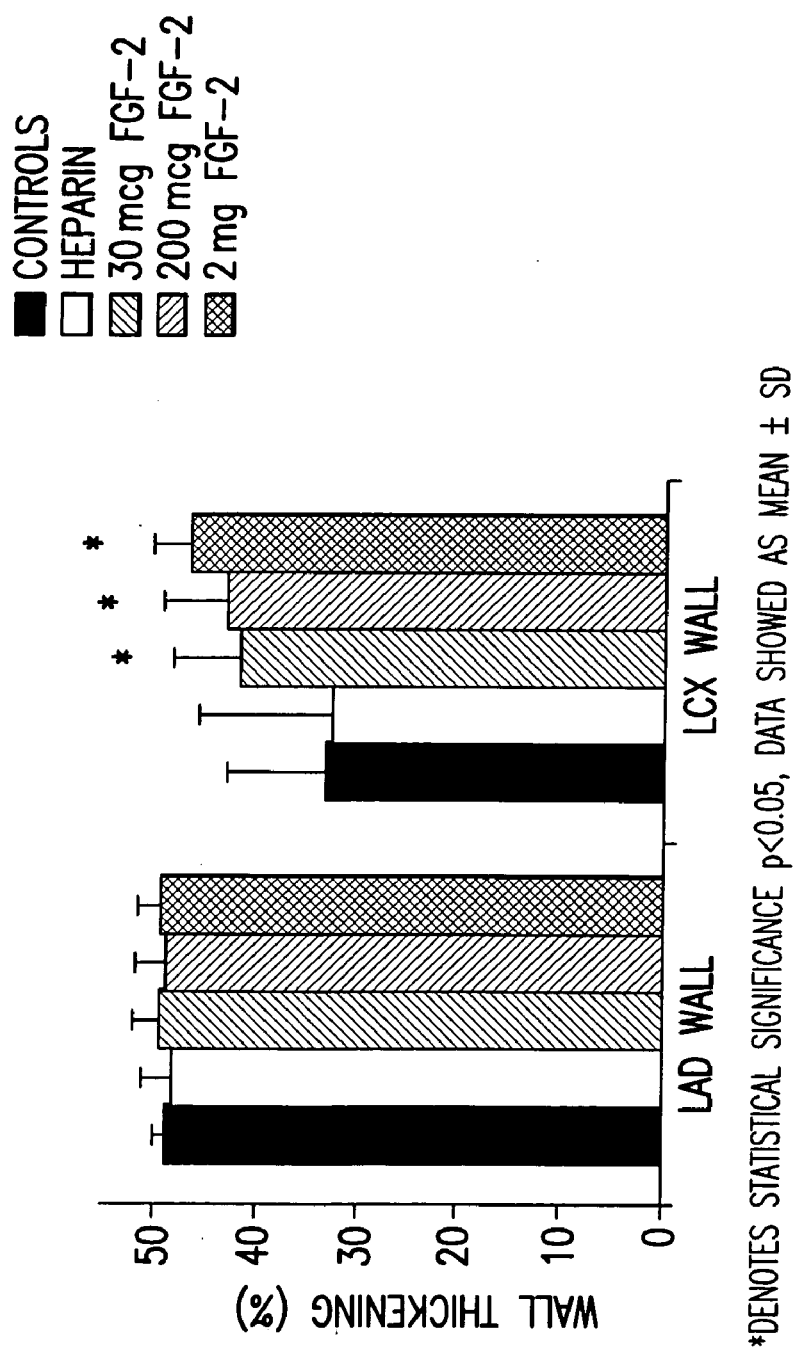

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens

<400> SEQUENCE: 1
cagtgtccaa catgctgctg gaaattg                                          27

<210> SEQ ID NO 2
<211> LENGTH: 22
<212> TYPE: DNA
<213> ORGANISM: Homo sapiens

<400> SEQUENCE: 2
taaaggtctt cttggtgatg cc                                               22

<210> SEQ ID NO 3
<211> LENGTH: 17
<212> TYPE: DNA
<213> ORGANISM: Homo sapiens

<400> SEQUENCE: 3
gcctcgctct ggaaaga                                                     17

<210> SEQ ID NO 4
<211> LENGTH: 17
<212> TYPE: DNA
<213> ORGANISM: Homo sapiens

<400> SEQUENCE: 4
tccatgcaga caacctt                                                     17
```

METHODS OF USE OF FIBROBLAST GROWTH FACTOR, VASCULAR ENDOTHELIAL GROWTH FACTOR AND RELATED PROTEINS IN THE TREATMENT OF ACUTE AND CHRONIC HEART DISEASE

REFERENCE TO RELATED APPLICATIONS

This application claims priority under Title 35, U.S.C. § 119(e) of U.S. application Ser. No. 60/195,624, Filed Apr. 6, 2000.

FIELD OF THE INVENTION

The present invention relates generally to strategies and methods for the treatment of chronic and acute heart disease through the delivery of one or more related protein growth factors such as fibroblast growth factor (FGF) and vascular endothelial growth factor (VEGF).

BACKGROUND OF THE INVENTION

Chronic myocardial ischemia is the leading cardiac illness affecting the general population in the Western world. Since the occurrence of angina symptoms or objective physiological manifestations of myocardial ischemia signifies a mismatch between myocardial oxygen demand and the available coronary blood flow, the goal of therapy is to restore this balance. This can be achieved either by attempting to prevent further disease progression through modification of risk factors, or by more aggressive modes of therapy such as reducing the myocardial oxygen demand (i.e. reducing the heart rate, myocardial contractility or blood pressure) by using anti-anginal medications, or by restoring the blood supply by means of mechanical interventions such as percutaneous transluminal angioplasty or its variants, or coronary artery bypass surgery, coronary angioplasty (PTCA) or bypass surgery (CABG). When CABG is selected as the treatment option, its success may be limited by the inability to provide complete revascularization in those patients in whom the artery that supplies a viable but underperfused myocardial territory is not graftable because of diffuse disease, calcifications, or small size. Complete revascularization cannot be achieved in up to 37% of patients undergoing CABG. This number is probably much lower today. However, patients who undergo complete revascularization have improved 5-year survival and angina-free survival compared with patients who have incomplete revascularization. Therefore, an adjunctive treatment strategy is warranted in patients undergoing CABG if complete revascularization is not possible. Percutaneous catheter-based revascularization is often precluded secondary to the same attributes that made the myocardial territory ungraftable: diffuse disease and small or calcified vessels.

The field of angiogenesis research was initiated 30 years ago by a hypothesis that tumors are angiogenesis-dependent. Folkman, J. "Tumor angiogenesis: therapeutic implications." *N. Engl. J. Med.* 285: 1182–1186 (1971). Shortly thereafter, in the early 1970's, it became possible to passage vascular endothelial cells in vitro for the first time. Bioassays for angiogenesis were developed subsequently through that decade. The early 1980's saw the purification of the first angiogenic factors. Clinical applications of angiogenesis research are being pursued along three general lines: 1) prognostic markers in cancer patients; 2) anti-angiogenic therapy (in cancer treatment); and 3) angiogenic therapy (treatment of heart disease).

In discussing the field of angiogenesis, it is important to differentiate 3 different processes that contribute to the growth of new vessels. Vasculogenesis is the primary process responsible for the growth of new vasculature during embryonic development, and it may play an as yet undefined role in mature adult tissues. Arteriogenesis refers to the appearance of new arteries possessing fully developed tunica media, while true angiogenesis describes the growth of collateral-like vessels lacking the development of media. In the case of coronary circulation, arteriogenesis is usually taken to mean new, angiographically visible epicardial vessels while angiogenesis refers to thin-walled intramyocardial collaterals.

Occlusion of coronary arteries is often associated with development of collateral circulation in patients with atherosclerosis. Although the existence of collateral circulation in such patients is associated with improved clinical outcomes, the net effect is rarely adequate to compensate fully for the flow lost to occlusion of native epicardial coronary arteries. A number of growth factors have been associated with myocardial and peripheral limb ischemia, particularly basic fibroblast growth factor (bFGF), acidic fibroblast growth factor (FGF-1), and vascular endothelial growth factor (VEGF), which have been shown to induce functionally significant angiogenesis in animal models of myocardial and limb ischemia. These promising preclinical results have rapidly lead to the study of these growth factors in patients with chronic myocardial ischemia using intracoronary (IC), intravenous (i.v.), and local delivery (myocardial injection).

Therapeutic myocardial angiogenesis is a novel approach to the treatment of myocardial ischemia based on the use of proangiogenic growth factors to induce the growth and development of new blood vessels to supply the myocardium at risk. Angiogenesis is a complex process involving endothelial and smooth muscle cell proliferation and migration, formation of new capillaries, and extracellular matrix turnover. Various heparin-binding growth factors, including basic fibroblast growth factor (FGF-2), acidic fibroblast growth factor, and vascular endothelial growth factor (VEGF) induce angiogenesis in chronic myocardial ischemia. Given the typically long time course of new collateral vessel development, most attempts to stimulate myocardial angiogenesis have used methods of prolonged growth factor delivery, including gene therapy, continuous infusions, repeated injections, or sustained release polymers. However, some of these options are not feasible or practical in patients with ischemic heart disease, making single dose administration, if effective, a potentially superior strategy in these patients.

Angiogenesis is a complex process that involves endothelial cell migration and proliferation, extracellular matrix breakdown, attraction of pericytes and macrophages, smooth muscle cell proliferation and migration, formation and "sealing" of new vascular structures, and deposition of new matrix. A number of growth factors, including the fibroblast growth factors (FGF) and vascular endothelial growth factors (VEGF) are integrally involved in the angiogenic response in ischemic conditions and in certain pathological states. The availability of these factors has led to studies, which have demonstrated a therapeutic benefit in various animal models of acute and chronic myocardial ischemia. In particular, basic fibroblast growth factor is an attractive candidate as an agent for therapeutic angiogenesis.

The therapeutic goal of attempting to ameliorate chronic ischemic conditions through revascularization by administration of various protein growth factors is feasible only due to the chronic nature of the condition and the resulting long-term time scale for treatment. In acute clinical situations, such as myocardial infarct, or therapeutic procedures likely to lead to reperfusion injury, the luxury of long time scales for revascularation is not available. However, the administration, via various routes, of growth factors such as FGF has been demonstrated to be effective in reducing the effects of myocardial infarct within a time frame that precludes a therapeutic contribution from the angiogenic function of these proteins. See, for example, my earlier U.S. Pat. No. 4,296,100, the disclosure of which is hereby incorporated specifically by reference. Thus, by a mechanism yet to be elucidated, protein growth factors such as FGF and VEGF and related proteins are capable of demonstrating a therapeutic utility in situations involving acute damage to the heart.

SUMMARY OF THE INVENTION

In a first embodiment, the present invention provides a method for the systematic, multi-tiered treatment of heart disease by delivery of therapeutic growth factor proteins comprising the steps of a.) selecting a patient displaying symptoms of heart disease; b.) administering at least one dose of an effective amount of a first therapeutic growth factor protein formulation by oral inhalation; c.) monitoring levels of CPK-MB in the patient; d.) determining whether administration of the growth factor protein formulation was effective in treating the symptoms of heart disease in the patient; e.) administering one or more additional doses of a second growth factor protein formulation by a method of delivery more invasive than delivery by oral inhalation; and f.) repeating steps c.) through e.) until there is a clinical indication of amelioration of the symptoms of heart disease in the patient, or until there is a contraindication to continued treatment. Preferably, the protein formulation comprises a growth factor protein selected from the group consisting of FGF-1, FGF-2, VEGF, and mixtures thereof. In one aspect of this embodiment, the method of the invention contemplates application where the symptoms of heart disease are acute. These acute symptoms of heart disease can be brought on by a condition selected from the group consisting of myocardial infarct, unstable angina, an acute anginal attack, and reperfusion injury. Furthermore, the reperfusion injury is induced by a procedure selected from the group consisting of thrombolytic therapy, bypass surgery and angioplasty. Alternatively, the method of the present invention contemplates applicatin where the symptoms of heart disease are chronic.

In an alternative embodiment, the method of the present invention encompasses the administration of therapeutic amounts of a growth factor protein formulation in the treatment of heart disease by delivering the protein formulation by inhalation therapy. Preferably, in the practice of the present invention, the protein formulation is a dry powder formulation. Alternatively, the protein formulation is a liquid aerosol formulation.

In another embodiment, the present invention provides a method for monitoring clinical effectiveness of administration of a growth factor protein formulation in the treatment of heart disease, the method comprising the steps of obtaining a sample of a biological fluid from a patient displaying symptoms of heart disease; performing an assay of the biological fluid to determine an amount of CPK-MB present in the fluid; administering a therapeutic amount of a growth factor protein formulation to the patient; and repeating the last two steps until the assayed amount of CPK-MB in the biological fluid has decreased by an amount sufficient to indicate the clinical effectiveness of the administration of the growth factor protein formulation.

BRIEF DESCRIPTION OF THE DRAWINGS

Figure 1:
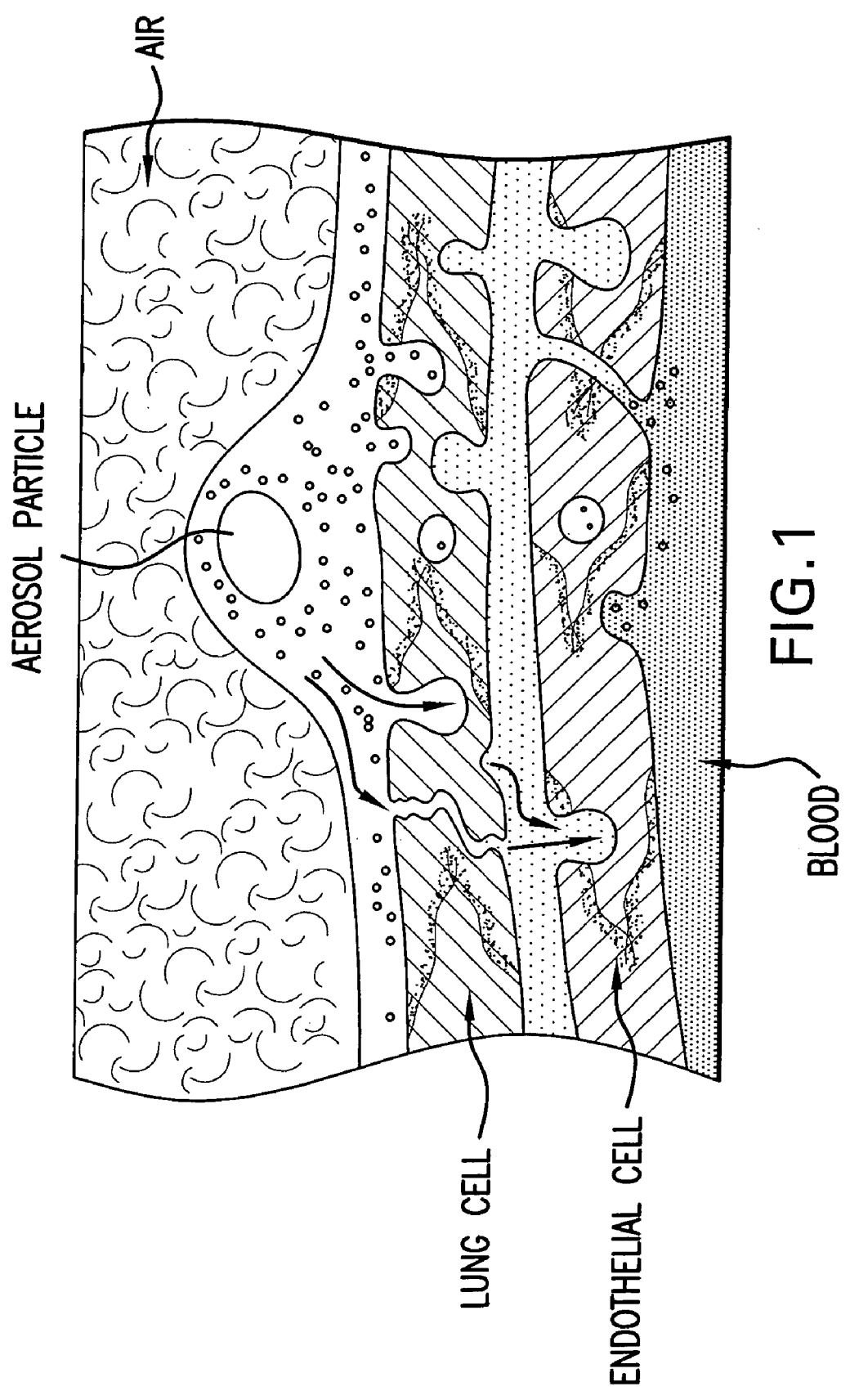

FIG. 1 is an illustration of the lung, indicating a mechanism of delivery of aerosol drug particles through the lung and into the bloodstream.

FIG. 2 is an illustration of the results of measured regional wall thickening in the LAD (normal) and LCX (collateral-dependent) distribution.

FIG. 3 is an illustration of, at top, MRI perfusion images of the left ventricle and, at bottom, the ischemic zone extent in all groups of test animals.

FIG. 4 is an illustration of histopathological sections from the LCX distribution demonstrating an increased number of capillaries in all treatment groups.

DETAILED DESCRIPTION OF THE INVENTION

Recent advances in growth factor therapy for the treatment of ischemic disease of the heart and peripheral vasculature offer hope of a novel treatment strategy that is based on generation of new blood supply in the diseased heart. Members of the fibroblast growth factor family, vascular endothelial growth factor family, and several other molecules have all been shown to result in functionally significant angiogenesis in animal models of acute and chronic myocardial and peripheral limb ischemia. The promising preclinical data have propelled the use of these angiogenic growth factors in clinical studies of ischemic heart and peripheral vascular disease. These growth factors are presumed to induce neovascularization by stimulating endothelial and smooth muscle cell proliferation and migration, dissolving the extracellular matrix, attracting pericytes and macrophages, and finally forming and "sealing" new vascular structures with deposition of new matrix.

In the surgical treatment of acute ischemic conditions, approximately 500 000 PTCA and 375 000 CABG procedures are performed annually in the United States. However, a significant number of patients are suboptimal candidates for CABG or PTCA or do not achieve complete revascularization with these procedures. These patients would likely benefit from additional measures to achieve enhanced revascularization, and therapeutic angiogenesis may serve this role. Several studies have demonstrated that chronic administration of FGF-2 results in significant myocardial angiogenesis in animal models of myocardial ischemia and infarction. However, because of the protracted time course required for new collateral vessel development, many attempts to stimulate myocardial angiogenesis have used methods of prolonged growth factor delivery, including gene therapy, continuous infusions, repeated injections, and sustained release polymers. Many of these therapeutic strategies, particularly those requiring repeated access or major surgical intervention, are impractical, or less than ideal, from a clinical standpoint. The pericardial space offers potentially unique advantages in convenience, safety, and efficacy as a cardiovascular drug depot site for the administration of proangiogenic growth factors.

In investigating the effects of a single intrapericardial injection of increasing FGF-2 doses in a porcine model of chronic myocardial ischemia, separate saline and heparin control arms were used to address the potential angiogenic effects of heparin alone or in combination with FGF-2. However, no significant differences were found between the heparin (at the dose used) and saline arms in any of the measured parameters. Intrapericardial FGF-2, on the other hand, resulted in an improvement in left-to-left angiographic collaterals, occluded LCX coronary artery blood flow, LCX (ischemic territory) myocardial perfusion, and LCX regional wall function as measured by MRI. Improvements in ischemic territory regional wall function and myocardial perfusion were positively correlated with FGF-2 dose, with near normalization of wall function and perfusion in the 2 mg FGF-2 group. Qualitative histopathologic examination showed increased myocardial vascularity in FGF-2-treated animals without any adverse findings.

In considering growth factor-induced neovascularization, it is important to distinguish intramyocardial collateral development from formation of epicardial collaterals (neoarteriogenesis). The process of intramyocardial collateral development (angiogenesis) is characterized by appearance of thin-walled vessels with poorly developed tunica media generally under 200 µm in diameter and by an increase in the number of true capillaries (<20 µm in diameter containing only a single endothelial layer), whereas the neoarteriogenesis is characterized by development of larger vessels (>200 µm in diameter) with well developed tunica media and adventitia that usually form close to the site of the occlusion of a major epicardial coronary artery (bridging collaterals) or extend from one coronary artery to the other. The distinction between these two groups of newly formed vessels is important not only from the point of view of their location but also because stimuli for their development appear to be quite different and because they may exhibit different physiological properties. It is unclear whether intrapericardially administered FGF-2 exerts its beneficial effects on myocardial revascularization by acting on the epicardial surface (where it is in greatest concentration) to induce collateralization around sites of occlusion in the epicardially situated major coronary arteries, or whether it diffuses into the myocardium and myocardial microcirculation to induce angiogenesis at a more microscopic level, or both. However, the demonstrated effectiveness of the low-dose (30 µg) intrapericardial FGF-2 suggests that the presence of FGF-2 on the epicardial surface may play a key role in inducing functionally significant angiogenesis.

Fibroblast Growth Factors

Acidic fibroblast growth factor (aFGF), also referred to as FGF-1, is a monomeric, acidic protein of approximately 18 kDa. It shares about 55% homology with the basic protein FGF-2. Both are prototypes for the FGF family members and their three dimensional structure are known.

Basic fibroblast growth factor (bFGF), also referred to as FGF-2, is a 16.5 Kd 146 amino acid protein that belongs to the FGF family, which now comprises more than 22 structurally related polypeptides. One of the key differences between the various FGFs is the presence or absence of the leader sequence required for conventional peptide secretion (absent in FGF-1 and FGF-2). Another difference is the varied affinity for the different isoforms of FGF receptors. As for most heparin-binding growth factors, bFGF binds with high affinity to cellular heparin sulfates and, with even higher affinity, to its own tyrosine kinase receptors (FGF receptors 1 and 2). The ability of bFGF to bind cell surface and matrix heparin sulfates serves both to prolong its effective tissue half-life and to facilitate its binding to its high affinity receptors. While bFGF is present in the normal myocardium, its expression is stimulated by hypoxia and hemodynamic stress.

FGB-2 is a pluripotent mitogen capable of stimulating migration and proliferation of a variety of cell types including fibroblasts, macrophages, smooth muscle and endothelial cells. In addition to these mitogenic properties, FGF-2 can stimulate endothelial production of various proteases, including plasminogen activator and matrix metalloproteinases, induce significant vasodilation through stimulation of nitric oxide release and promote chemotaxis. FGF-2 is present in the normal myocardium and its expression is potentiated by hypoxia or hemodynamic stress. Because of its heparin-binding properties, FGF-2 binds avidly (Kd $10^{-9}$M) to endothelial cell surface heparin sulfates. This interaction serves to prolong effective tissue half-life of the FGF-2 protein, facilitates its binding to its high-affinity receptors and plays a key role in stimulation of cell proliferation and migration. BFGF also possesses a plethora of other biological effects such as the ability to stimulate NO release, to synthesize various proteases, including plasminogen activator and matrix metalloproteinases, and to induce chemotaxis. Homozygous deletion of the bFGF gene is associated with decreased vascular smooth muscle contractility, low blood pressure and thrombocytosis. One interesting aspect of bFGF is its biological synergy with VEGF. Thus, a combination of BFGF and VEGF is far more potent than bFGF alone in inducing angiogenesis in vitro and in vivo. Furthermore, bFGF induces VEGF expression in smooth muscle and endothelial cells.

Despite significant levels of bFGF in normal tissues, the growth factor does not appear to be biologically active, as suggested by the lack of on-going angiogenesis. While the precise explanation for this lack of activity of the endogenous bFGF is uncertain, contributing factors probably include very low levels of expression of FGF receptors 1 and 2 and syndecan-4, another transmembrane protein involved in bFGF-dependent signaling. In addition, endogenous bFGF may be sequestered in the extracellular matrix by binding to heparin sulfate-carrying proteoglycan percelan and, thus, be unavailable to bind to its signaling receptors.

Vascular Endothelial Growth Factor

Similar to bFGF, vascular endothelial growth factor (VEGF) transcripts are detected in all cardiac tissues. VEGF and the expression of its receptors in the heart are induced 7-fold by hypoxia/ischemia. The unique feature of VEGF was thought to be the narrow spectrum of activity, presumed to be confined to endothelial cells because of the restricted expression of its receptors. However, recent studies suggest VEGF receptor expression is more widespread and includes monocytes and some smooth muscle cells. Furthermore, VEGF is capable of inducing bFGF expression, thereby further increasing its biological spectrum of activity. VEGF is a potent and specific mitogen for vascular endothelial cells that is capable of stimulating angiogenesis during embryonic development and tumor formation. The VEGF family of structurally related growth factors has five mammalian members, VEGF, VEGF-B, VEGF-C, VEGF-D, and placenta growth factor (PIGF), all encoded by separate genes. Stacker, S. A. and Achen, M. G. "The vascular endothelial growth factor (VEGF) family: signaling for vascular development." *Growth Factors* 17: 1–11 (1999).

Fibroblast Growth Factor (FGF), in its human and bovine basic forms, and in its human acidic form, has been used successfully to treat ischemic heart disease, including chronic angina, by stimulating angiogenesis (the growth of new blood vessels). Vascular Endothelial Growth Factor (VEGF) has also been used to treat ischemic heart disease by stimulating angiogenesis. FGF has been demonstrated to show a reduction in acute myocardial infarct size after treatment. Treatment of myocardial infarct (MI) requires acute intervention by health care professionals, whereas angiogenesis may take at least several days to occur to a sufficient extent to demonstrate any clinical benefit in the affected patient. It is the purpose of this invention to utilize a form of FGF and/or VEGF, or other related growth factor proteins, to bring immediate relief from MI, unstable angina, or an anginal attack and then, utilizing the same or an alternate delivery system, to promote angiogenesis for the relief of subacute or more chronic symptoms.

Angiogenesis begins when blood-starved areas of the heart send out receptor signals. The purpose of this invention is achieved by administration to the affected patient of an effective amount of a form of FGF and/or VEGF via inhalation delivery techniques. Inhalation treatment with FGF and/or VEGF for the management of coronary artery disease should be successful because the lung is one of the least blood or oxygen starved organs. The FGF or VEGF would end up on the left atrium of the heart and from there travel to the coronary arteries where it would be most useful. The inhalation of FGF and/or VEGF into the lungs could be used for the treatment of MI, unstable angina, or an anginal attack. This delivery system could also be used before, during, and/or after thrombolytic therapy (such as administration of recombinant tissue plasminogen activator) to help alleviate ischemic or reperfusion injury.

After successful treatment of acute myocardial infarct or acute ischemia via the methods of the present invention, angiogenesis may also occur. If it does not occur within two or three weeks, then the inhalation therapy could be repeated or the FGF and/or VEGF could be given through a catheter into the coronary arteries or by direct injection in the left atrium, or ventricular myocardium via a limited thoracotomy. For the treatment of acute myocardial infarct (with or without thrombolytic therapy), unstable angina or an anginal attack, the least invasive method would be preferred. Besides inhalation into the lungs, other available methods of delivery could be sublingual, intranasal, or IV utilizing one of the forms of FGF and/or VEGF. If the least invasive approaches are not successful in the treatment of acute myocardial infarct or acute ischemic, then alternate deliver systems should be explored. As clinically indicated, the FGF and/or VEGF could be given through a catheter into the coronary arteries or by direct injection into the left atrium or ventricular myocardium via a limited thoracotomy. To assess the efficacy of VEGF or FGF in the treatment of acute myocardial infarct or unstable angina, you could follow levels of creatine phosphokinase-myocardial band (CPK-MB) isoenzymes. Even a minimal elevation above normal range would be considered significant. With treatment, the rise in the level should be less when compared to placebo.

Alternative methods of delivery for treatment of coronary artery disease should also be considered. FGF and/or VEGF could be administered directly into the myocardium during transmyocardial laser revascularization, into the coronary arteries during angioplasty, or by injection into the coronary arteries, myocardium or bypass grafts during coronary bypass surgery. When injected into the myocardium, slow release forms of FGF or VFGF should be considered. It might also be possible to inject FGF and/or VFGF into the myocardium via a catheter passed during cardiac catheterization.

To promote angiogenesis for the relief of chronic angina or ischemia the least invasive method would be preferred. The inhalation of FGF and/or VEGF into the lungs could be used to achieve this goal. Besides inhalation into the lungs, other available methods of delivery could be sublingual, intranasal, or IV utilizing one of the forms of FGF and/or VEGF. If the least invasive approaches are not successful in promoting angiogenesis, then alternate delivery systems should be explored. As clinically indicated the FGF and/or VEGF could be given through a catheter into the coronary arteries or by direct injection into the left atrium or ventricular myocardium via a limited thoracotomy.

Methods of Delivery of Growth Factors

Despite promising preclinical data, the progression of angiogenic growth factor therapy to the clinical trials stage awaits a practical delivery strategy. This requirement essentially eliminates all forms of prolonged or frequent repetitive intracoronary infusions. Local perivascular delivery is more easily adaptable to clinical trials, but it requires open-chest surgery. One such form of delivery is heparin alginate capsules that provides prolonged (4 to 5 weeks) first-order kinetics release of the growth factor from the polymer. The capsules are easily implanted and do not provoke an inflammatory response. One potential advantage of perivascular delivery is the absence of the endothelial barrier and the absence of the rapid washout that is typical with intravascular administration.

The pericardial space may potentially serve as a drug delivery reservoir that might be used to deliver therapeutic agents to the heart. Chronic intrapericardial FGF-2 delivery in a rabbit model of angiotensin 11-induced cardiac hypertrophy resulted in a localized myocardial angiogenic response. A single intrapericardial injection of FGF-2 with or without heparin resulted in localized angiogenesis and myocardial salvage in a canine model of myocardial infarction. Moreover, the concentration of FGF-2 and VEGF in the pericardial fluid of patients with unstable angina has been documented to be higher than that in patients with nonischemic heart disease, suggesting that increases in the levels of proangiogenic growth factors in the pericardial space may reflect an endogenous and, indeed, physiological response to myocardial ischemia and injury. Accordingly, the pericardium may serve as a useful reservoir for proangiogenic growth factor administration in patients with coronary disease.

An alternative approach to perivascular administration of bFGF involves intrapericardial delivery of the growth factor. A major advantage of this approach is that it can be accomplished via a catheter, obviating the need for open-chest surgery. However, the clinical application of intrapericardial delivery is limited to a small number of patients currently being enrolled in coronary angiogenesis trials because of the high prevalence (80 to 90%) of prior coronary artery bypass surgery in this group of patients.

The feasibility of short duration intracoronary or intravenous infusions and endomyocardial injections has also been tested in animal models. Intravenous infusions are appealing because of their practicality, low cost and applicability to a broad group of patients. Furthermore, treatment can be easily repeated and may not require any special facilities. The downside includes systemic exposure to a growth factor and the potential for adverse effects such as NO-mediated hypotension.

Intracoronary infusions are easily carried out in any cardiac catheterization laboratory and are also applicable in most patients with coronary disease. However, the need for left heart catheterization limits this approach to a single session or, at most, infrequent repetitions. While somewhat more "local" than intravenous infusions, intracoronary infusions are also likely to result in systemic exposure to the growth factor and may precipitate systemic hypotension. A variation on the same theme is transvascular intracoronary administration with a local delivery catheter. This approach, while it is potentially feasible, remains experimental at this time, and it is still associated with significant systemic recirculation.

Detailed evaluation of tracer-labelled growth factor uptake and retention in the myocardium, and its systemic distribution following intracoronary and intravenous infusions, demonstrated that both forms of delivery are associated with relatively low uptake in the target (ischemic) area of the heart. Thus, at 1 hour after injection, 0.9% of the injected bFGF was found to be present in the ischemic myocardium following intracoronary administration and 0.26% following intravenous administration. Perhaps more importantly, 24 hours later, very small amounts of the growth factor remained in the myocardium (0.05% for intracoronary and 0.04% for intravenous administration).

Intramyocardial delivery of growth factors is the least evaluated form of therapy at this time. The appeal of this mode of delivery includes the possibility of targeting the desired areas of the heart, which is likely to provide higher efficiency of delivery and prolonged tissue retention. The drawbacks are its invasive nature, and requirements for highly specialized equipment and a high skill level for the operator. Furthermore, no conclusive data regarding the physiological efficacy of this mode of administration are available to date.

The pharmacokinetics and tissue distribution of protein growth factors administered by various techniques have not been clearly defined. Although an i.v. delivery strategy is very appealing in terms of technical safety, ease of administration, and lack of need for cardiac catheterization, it is unclear whether i.v. delivered growth factors achieve therapeutic myocardial concentrations without untoward systemic effects. In addition, IC infusions may not result in more significant myocardial deposition and retention with the added invasiveness of the delivery technique. The relevance of tissue distribution becomes apparent when one considers the potential systemic toxicity of these agents in terms of hemodynamic effects, recirculation, and organ deposition, with the potential to induce pathologic angiogenesis and tumor genesis.

Pulmonary Routes of Administration Pulmonary delivery of potentially therapeutic agents provides a direct route to the circulation, with a minimum of discomfort and pain, and is a cost-effective alternative in comparison to the more invasive routes of delivery typically utilized for administration of FGF, VEGF, and related proteins. Traditionally, noninvasive delivery systems do not work for macromolecules; pills or tablets enter the stomach, where enzymes and hydrochloric acid rapidly degrade the protein or peptide. The oral administration of proteins and peptides is under investigation, but no satisfactory system is commercially available yet. No acceptable transdermal delivery systems have been found because of proteins' size constraints or inherent physical properties that prohibit these large molecules from crossing the diverse layers of the skin without the addition of irritating enhancers.

The biology of the lung makes it a favorable environment for noninvasive drug delivery (see FIG. 1). Studies have shown that most large-molecule agents are absorbed naturally by the lungs, and once absorbed in the deep lung, they pass readily into the bloodstream without the need for enhancers used by other noninvasive routes. Patton, J. S. *Adv. Drug Delivery Rev.* 1996, 19, 3. On inhalation, air passes through the trachea, which branches more than 17 times into successively smaller tubes that constitute the bronchial network, eventually reaching the grapelike clusters of tiny air sacs known as alveoli. Each breath of air is distributed deep into the lung tissue, to the alveolar epithelium, the surface area of which measures ~100 $m^2$ in adults—roughly equivalent to the surface area of a standard singles tennis court. This large area is made up of about half a billion alveoli, from which oxygen passes into the bloodstream via an extensive capillary network.

The potentially most significant barrier to the delivery of compounds via the lungs is the tightly packed, single-cell-thick layer known as the pulmonary epithelium. In the lungs, the epithelium of the airway is very different from that of the alveolus. Thick, ciliated, mucus-covered cells line the surface of the airway, but the epithelial cell layer thins out as it reaches deeper into the lungs, until reaching the tightly packed alveolar epithelium. Most researchers believe that protein absorption occurs in the alveoli, where the body absorbs peptides and proteins into the bloodstream by a natural process known as transcytosis.

Logically, there is no reason to expect safety problems related to the inhalation of a substance to be any different from those associated with the injection of the same amount of the substance. A growing quantity of safety data indicates that inhaling proteins can be safe for patients with healthy or diseased lungs. The safety of therapeutic inhalation is further supported by the existence of more than 20 small-molecule and one large-protein drug inhalation products approved by the U.S. Food and Drug Administration (FDA); this group of therapeutic inhalants contains 13 different excipients.

Most aerosol systems today deliver a total amount of <100 μg of drug per puff to the deep lung; this amount is too low to enable timely delivery of many macromolecules if the required dose is in the milligram doses. Traditional inhalation systems have been designed primarily to deliver some of the most potent drugs in use today, the bronchodilators and bronchosteroids to treat asthma. Both types of compounds are bioactive in the lung at 5–20 μg per dose. In contrast, many peptide and protein compounds need to be delivered to the deep lung at much larger doses of 2–20 mg. Adjei, A. L.; Gupta, P. K. *Inhalation Delivery of Therapeutic Peptides and Proteins*; Marcel Dekker: New York, 1997.

Bioavailability After the aerosolized drug reaches the deep lung, it must be absorbed with high enough bioavailability to make the system practical. As early as 1925, insulin inhalation for the treatment of diabetes was shown to work in humans, but the bioavailability was low (<3%). More recently, several inhalation studies comparing insulin administration by aerosol inhalation (using cumbersome devices) and by subcutaneous injection for the reproducibility of dosing have shown that the variability in glucose response to the two methods was equivalent. Bioavailability in more recent studies with aerosol insulin was up to 25%, supporting the use of such a method of administration. Laube, B. L.; Georgopolos, A.; Adams, G. K. *J. Am. Med. Assoc.* 1993, 269, 2106. Insulin administered by oral inhalation effectively normalized diabetic patients' plasma glucose levels without adverse effects. Numerous patents have issued, directed to methods, formulations and devices for the oral administration of insulin via inhalation therapy. See, for example, U.S. Pat. Nos. 5,952,008; 5,858,968; and 5,915, 378, the disclosures of which are hereby incorporated specifically by reference.

Bioavailability studies in humans of the aerosol administration of lutenizing hormone-releasing hormone (LHRH), a decapeptide, and its analogues also have demonstrated that appropriate bioactive systemic levels can be achieved to treat conditions such as endometriosis and prostate cancer. Thus, using delivery and formulation technology available today, as would be recognized by one of skill in the appropriate art, it will be possible to deliver an effective amount of FGF and/or VEGF, and related growth factor proteins, in the treatment of chronic and acute heart disease.

The mechanism of macromolecule absorption in the deep lung is thought to occur via normal physiological processes that can deliver active compounds with relatively high bioavailability without requiring the addition of penetration enhancers. LHRH analogues (used in treating osteoporosis), composed of 10 amino acids, can reach 95% bioavailability; however, interferon-$\alpha$ (used in treating hepatitis B and C), composed of 165 amino acids, attains 29% bioavailability. Some smaller peptides such as glucagon (29 amino acids) and somatostatin (28 amino acids) reach 1% bioavailability. The degree of bioavailability is thought to depend on the peptide or protein susceptibility to certain hydrolytic enzymes in the lung.

How a macromolecular drug is formulated also affects its delivery to the deep lung. Many macromolecules are formulated as dry powders because they are more stable as solids than as liquids. Compared with liquid aerosol particles, which are mostly water (97%), dry powder aerosol particles can carry 50–100% of the drug. In general, more puffs would be necessary to deliver the equivalent amount of drug to the alveolar epithelium from a liquid aerosol device. Liquid formulations also carry the risk of microbial growth; the risk of lung infections due to bacterial and fungal contaminants is greatly reduced with dry powder systems. By greatly lowering the possibility of microbial contamination, dry powder systems offer a safer technology.

In the liquid state, individual protein or peptide molecules are extremely mobile. When water is removed, macromolecules usually pack together in an amorphous state, unlike the highly ordered packing that occurs in crystallization. When water is removed from proteins, the protein molecules remain mobile and chemical stability stays low in the initial amorphous powder that forms. When a critical amount of water has been removed, a kind of molecular gridlock occurs, producing a greatly increased chemical stability called the "amorphous glass state." In this state, previously mobile molecules slow down drastically. As long as the glass transition temperature of the powder is higher than any environmental temperatures that may occur during normal human use, the powder will remain in a glass state.

Systematic, Multi-Tiered Approach to the Use of Growth Factor Proteins in the Treatment of Acute and Chronic Heart Disease.

Of the various treatment modalities currently in use or under investigation for the delivery of therapeutically effective doses of various growth factor proteins, a wide range of levels of invasiveness are involved. Obviously, intravenous administration is among the least invasive, but questions remain as to the ultimate delivery of the proteins to physiological sites at therapeutically effective levels. Next most invasive is intracoronary infusion through catheters. Although requiring surgical intervention, the insertion and manipulation of catheters has seen increasingly widespread use in the treatment of the symptoms of heart disease and a number of other clinical conditions. However, for most, if not all, cardiac patients, there is a very low level of toleration of such catheterizations procedures, so that the possibility of repeated deliver of growth factor proteins is extremely limited.

Next on the relative scale of invasiveness is intrapericardial injection of growth factors. Although requiring more substantive surgical procedures, this technique can be utilized in conjunction with other surgical procedures such as coronary artery bypass surgery and would, thus, not constitute an additional traumatic burden on the patent. Alternatively, relatively minor incisions can be made in the chest wall to permit direct interpericardial delivery. Again, due to the invasive nature of the procedures utilized in this manner of delivery, the realistic possibility of repeated administration via this route is very low.

At the most invasive end of the spectrum is direct myocardial injection of FGF and related proteins. This, of course, requires open heart surgery to achieve access to the delivery site. As such, this approach is feasible only when used in conjunction with surgical intervention for other purposes, such CABG. Again, the major drawback here is that there is very little practical opportunity for repeated delivery of the therapeutic protein.

At the opposite end of the invasiveness spectrum, intrapulmonary inhalation therapy, preferably via dry powder formulations, offers significant advantages over previous delivery strategies. As discussed above, formulation and delivery technology has reached a state where a number of therapeutic macromolecules, including insulin, can now be delivered consistently, and at clinically effective levels via inhalation therapy. An added advantage arising from the non-invasive nature of inhalation therapy is that it is particularly attractive in the treatment of chronic heart conditions that require repeated dosing over longer time intervals. The non-invasive nature of the therapy also proves to be of significant advantage in the treatment of acute heart conditions such as the onset of a myocardial infarct. For patients known to be at risk for such a cardiac event, it will be possible to carry a relatively compact dry powder inhalation device so that at the onset of symptoms, the patient can self-administer a dose of growth factor that may prove to be significantly effective in reducing the damage induced by the MI, and may eventually prove to constitute the difference between life and death.

Recognizing the scope of therapies potentially available in the treatment of both acute and chronic heart disease, it is therefore an aspect of the present invention to provide a systematic, multi-tiered therapeutic approach to the administration of FGF, VEGF and related growth factor proteins. This approach must, of necessity, recognize the relative invasiveness of different treatment modalities, and the likelihood of repeated recourse to such treatment procedures.

In implementing the rational, multi-tiered therapeutic approach of the present invention, it is recognized that differing approaches need be taken with respect to chronic and acute conditions. In the case of chronic conditions, the initial tier of therapeutic treatment is the administration of therapeutic levels of FGF (acidic or basic), VEGF, or related growth factor proteins, either individually or in combination, via dry powder inhalation therapy. Ideally, this therapy should be utilized as soon as possible after the onset of acute symptoms. For this form of delivery, repeated doses can be administered, at levels and at dosage ranges as set forth in the examples below.

Upon appropriate monitoring of the clinical effectiveness of the initial tier of therapy, as disclosed herein, the health practitioner can assess the advisability of proceeding to the next tier of interventional therapy. As described above, the next most invasive level of therapy would entail the intracoronary delivery, via catheter, of therapeutic doses of one or more of the growth factor proteins. As alluded to above, in the acute stage of heart disease, the health practitioner does not have the option of a great deal of time in which to assess the success of alternative treatment options. Thus, the ability to assess, short-term, the efficacy of a particular treatment is essential to formulating the overall therapeutic strategy. The methods of the present invention, disclosed below, for assessing on a short term basis the effectiveness of growth factor protein treatment are essential to the rational, multi-tiered approach to the treatment of heart disease disclosed and claimed herein.

Upon assessment that the clinical effectiveness of intracoronary delivery of the protein growth factor has not met the desired therapeutic goal, the health care provider must consider options involving far more invasive surgical intervention. Among these would be the intra-pericardial injection of FGF, VEGF, and/or other related protein growth factors. If the health care provider has reached the point in assessment of therapeutic options where coronary angioplasty (PTCA) or bypass surgery (CABG) is mandated, then the delivery of one or more growth factor proteins becomes feasible. At this level of therapy, for patients whose condition does not require PTCA or CABG, but whose response to previous levels of therapy has not been adequate, an alternative option is to utilize a limited thoracotomy for intrapericardial delivery of the therapeutic protein(s).

At a final level of therapeutic intervention, FGF or other protein may be delivered by direct injection into the myocardium during transmyocardial laser revascularization, or during coronary bypass surgery. At this level of treatment, it is also possible to implant slow-release beads comprising the therapeutic protein for both long- and short-term benefit.

An additional aspect of the treatment of acute symptomatic conditions is that, unlike uncontrollable incidents arising from unstable angina, acute anginal attacks, or onset of myocardial infarct, certain therapeutic procedure have the potential to create symptoms that can be alleviated through administration of FGF, VEGF, and/or related proteins. Specifically, reperfusion injury can occur during any procedure when blood flow is temporarily curtailed or restricted, upon reinstitution of full blood flow. Examples would be in the course of thrombolytic therapy (such as the administration of recombinant tissue plasminogen activator), as well as in bypass surgery and angioplasty. As the data included herein demonstrate, the extent of reperfusion injury that can result in such situations can be ameliorated through administration of FGF, VEGF, and/or related proteins prior to reinstatement of full blood flow. Thus, the rational, multi-tier therapeutic approach for the treatment of acute conditions of the present invention can be modified to include the administration of the appropriate growth factor protein or mixtures thereof prior to initiation of the procedure raising the risk of reperfusion injury.

The rational, multi-tier approach to treatment of heart disease with FGF, VEGF and/or related growth factor proteins can be adapted to treatments for chronic, as opposed to acute, conditions. The initial tier, as with acute conditions, is based on delivery of the therapeutic proteins via inhalation therapy, preferably using dry powder formulations. Thus, for patients exhibiting the symptoms of chronic ischemic disease, initial treatment involves inhalation therapy with a therapeutically effective amount and formulation of FGF, VEGF, and/or related proteins according to a dose level and dosing regimen as set forth in the Examples below. Due to the long-term nature of such conditions, the progress from less invasive to more invasive treatment modalities does not need to progress on a shortened time scale as is the case for treatment of acute conditions. Thus, multiple administrations of the protein(s) via inhalation therapy are possible, preferably accompanied by clinical evaluation of the effectiveness of previous treatments. In this fashion, dose levels and/or dose schedules can be adjusted based upon the results of periodic clinical evaluation of the presence of markers such as CPK-MB, as disclosed more fully below.

If the clinical evaluations do not reveal sufficient progress in amelioration of symptoms associated with the disease state, then the health care provider can move to the next tier, or level, of treatment, moving further along the spectrum of increasing invasiveness. Thus, the next tier would involve intracoronary perfusion via catheter. After a period of monitoring of the therapeutic effectiveness of the intracoronary perfusion, the health care provider can assess whether it will b necessary to move to the next, more invasive, tier of treatment. Assuming that the patient's condition has not responded to treatment to date, then it is likely that the health care provider will be forced to consider more invasive surgical treatments such as bypass surgery or coronary angioplasty. If clinical conditions dictate such an escalation of therapy, then the next tier of therapy, interpericordial injection of the growth factor protein(s) can be implemented in conjunction with the surgery. Alternatively, for patients whose condition does not warrant, or cannot support, angioplasty or bypass surgery, a limited thoracotomy may be used to achieve interpericordial delivery of the protein(s).

If symptoms or clinical testing do not evidence sufficient progress in treatment, then the health care provider may elect to move therapy to the highest tier of invasiveness. Thus, intermyocardial delivery of FGF, VEGF and/or related proteins may be achieved in conjunction with surgical procedures.

Integral with the rational, multi-tier approach of the methods of the present invention, is the use of a rapid, easily accomplished clinical evaluation procedure designed to provide the health care provider with an indication of the efficacy of growth factor therapy. Accordingly, the present invention provides an assay technique that satisfies this need. As one of skill in the relevant art would recognize, the criteria used to diagnose myocardial infarction (MI) can be of critical importance clinically. The most widely accepted diagnostic criteria for MI are those of the World Health Organization, first proposed over 20 years ago. These criteria require the presence of at least 2 of the following 3 criteria: (1) a history of ischemic-type chest discomfort; (2) evolutionary changes on serial electrocardiograms; and (3) a rise and fall in serum cardiac enzymes. Joint International Society and Federation of Cardiology/World Health Organization Task Force "Nomenclature and criteria for diagnosis of ischemic heart disease," *Circulation* 59: 707–709 (1979). Of importance here the use of creatine kinase (CK) and the more myocardium specific. MB isoenzyme, CK-MB, as markers for MI. Wagner, G. S. "Optimal use of serum enzyme levels in the diagnosis of acute myocardial infarction," *Arch Intern Med* 140: 33–38 (1982). Data compiled in conjunction with the large, multicenter Platelet Glycoprotein IIb/IIIa in Unstable Angina: Receptor Suppression Using Integrilin Therapy (PURSUIT) trial suggest that small CK-MB elevations represent clinically important evidence of myocardial necrosis and should be considered sufficient cardiac-marker criteria for a diagnosis of MI in patients with acute coronary syndromes. Alexander, J. H., et al., "Association Between Minor Elevations of Creatine Kinase-MB Level and Mortality in Patients With Acute Coronary Syndromes Without ST-Segment Elevation," *JAMA* 283: 347–353 (2000).

The conclusion to be drawn from this data is that monitoring of the level of CK-MB can provide useful information for the clinical practitioner is assessing the short-term efficacy of various levels of treatment with FGF, VEGF and/or related growth factor proteins. Thus, the method of the present invention contemplates implementation of a rational, multi-tier therapeutic treatment strategy for administration of growth factor proteins in patients with chronic and/or acute heart disease, preferably with periodic evaluation of CK-MB levels as a marker of the clinical efficacy of growth factor delivery, and as an indicator of the need to consider escalation of therapy to the next most invasive tier of treatment.

As would be recognized by one of skill in the appropriate art, methods and materials for the clinical monitoring of CK-MB levels are commercially available and are routinely practiced in the context of health care institutions.

EXAMPLES

Specific examples of the present invention are illustrated in the following Examples that are not to be construed as limiting of the scope of the claimed invention.

Example 1

Intracoronary Injection of FGF-2 in the Treatment of Severe Ischemic Heart Disease: A Maximally Tolerated Dose Study Patient selection. The study was conducted at two centers, the Beth Israel Deaconess Medical Center (Boston, Mass.) and Emory University Hospital (Atlanta, Ga.), and patients were enrolled between December 1997 and July 1998. The study was approved by the Institutional Review Boards at both hospitals. The inclusion criteria selected for patents with advanced CAD with inducible ischemia and who were considered to be suboptimal candidates for either PTCA or CABG. Patients were excluded from the study if they had any of the following criteria: uncompensated congestive heart failure or an ejection fraction <20%; a myocardial infarction within three months; new onset of angina or unstable angina within three weeks; PTCA, CABG, stroke or transient ischemic attack within six months; uncontrolled hemodynamically significant arrhythmias; critical valvular disease; restrictive or hypertrophic cardiomyopathy; arteriovenous malformations; proliferative retinopathy, retinal vein occlusion, or macular edema; renal insufficiency (creatinine clearance <80 ml/min by 24-h urine collection); vasculitis or chronic immunosuppressive therapy; or any malignancy within the past 10 years (except for curatively treated nonmelanoma skin cancer). Patients with diabetes mellitus were eligible if they had no proliferative retinopathy or severe nonproliferative retinopathy, and no microalbuminuria.

Patient population. Fifty-two patients met all eligibility criteria and received a single IC infusion of rFGF-2. The mean age was 60.8±10.1 years (range 41 to 80) and 2 of 52 patients were women. Six patients (11%) had diabetes mellitus and 31 patients (60%) had elevated cholesterol (serum cholesterol >200 mg/dl). Forty-three patients (83%) had a history of at least one prior CABG. The mean ejection fraction (evaluated by MR imaging) was 51.4±12.0% (range 20% to 73%). Sixty-nine percent of patients had NYHA class II or III symptoms of congestive heart failure.

Study design. This was an open-label interpatient dose escalation study. The initial dose of 0.33 g/kg was escalated over eight sequential groups to 48 g/kg IC. At least four patients were studied at each dose. If no patient experienced dose-limiting toxicity as defined by the protocol within six days, the dose was escalated; if one patient experienced dose-limiting toxicity, an additional four patients were studied at that dose. The MTD was defined as the dose tolerated by 9 of 10 patients.

Study procedures. After providing informed consent and meeting all eligibility criteria, patients underwent baseline evaluations that included a complete medical history and physical examination, an ophthalmologic examination with fundus photography read by a core laboratory using the Early Treatment Diabetic Retinopathy score (ETDRS), an exercise tolerance test (ETT), a Seattle Angina Questionnaire (SAQ), and nuclear and MRI cardiac scans. Measurement of initial health status allowed the use of change in scores, thus adjusting for differences in baseline health. Self-administration was used instead of telephone interview to minimize data collection bias.

On day 1, patients underwent right and left heart catheterization and coronary angiography. If the coronary anatomy was not amenable to PTCA or CABG, recombinant FGF-2 (rFGF-2, Chiron Corporation, Emeryville, Calif.) was infused with a Baxter pump through diagnostic catheters into two major conduits of myocardial blood supply over 20 min (10 min in each vessel) with continuous monitoring of systemic blood pressure and right atrial and pulmonary capillary wedge pressures, and cardiac output. In occasional patients the entire dose was infused into a single vessel that was believed to be the major source of blood supply. Prior to initiation of rFGF-2 infusion, normal saline was administered intravenously (i.v.), if required, to ensure mean pulmonary capillary wedge pressure >12 mm Hg. Heparin (40 U/kg) was administered i.v. more than 10 min before rFGF-2. The volume of infusion varied with dose and the patient's weight, ranging from 10 ml at lower does to 40 ml at higher doses.

The right heart (Swan-Ganz) catheter was left in place for 7 h following drug infusion to monitor filling pressures and cardiac output. Patients were monitored with full-disclosure telemetry for 24 h following rFGF-2 administration. Patients were discharged 24 h after study drug infusion and clinical follow-up visits were performed at days 6, 15, 29, 57, 180 and 360. Quality of life was assessed using the Seattle Angina Questionnaire at baseline and days 57 and 180. ETT's were obtained at days 29, 57 and 180. Exercise stressed nuclear perfusion scans (rest thallium/stress $^{99m}$Tc-sestamibi) and resting cardiac magnetic resonance scans were performed at days 29, 57 and 180.

Preliminary Efficacy of RFGF-2 Therapy. Although the small sample size and the absence of a control group preclude any definitive conclusions regarding efficacy, several findings suggest potential clinical benefits of intracoronary rFGF-2 administration. In particular, quality of life, as assessed by the SAQ, improved in treated patients at day 57 compared with baseline, and this improvement was sustained for six months. The magnitude of improvements in the five SAQ scales was similar to that seen following PTCA and CABG in patients with ischemic heart disease. There was also a significant improvement in exercise capacity, as measured by exercise treadmill testing, seen at days 57 and 180. Of note, there was minimal improvement at day 29. The late occurrence of improvement in exercise testing is in keeping with the assumed time course of coronary angiogenesis. However, the absence of a dose response tempers the preliminary efficacy seen in this study.

In addition, to these subjective measures of clinical status, resting MR imaging was performed to assess left ventricular function and myocardial perfusion. Using this approach, we detected no difference in overall left ventricular ejection fraction at any time during the study. However, there was a significant improvement in systolic thickening of the target wall at day 29, which was maintained at six months, and was paralleled by a significant reduction in the size of the ischemic myocardium as assessed by blood arrival imaging. Although cardiac MR imaging is considered the "gold standard" for evaluation of left ventricular function, its application to clinical trials in coronary disease is very limited. Similarly, despite recent advances in MR-based perfusion assessment of the myocardium, there has been no substantial clinical experience with this imaging modality. Prior animal studies have documented improvement in MR-assessed parameters of left ventricular function in the setting of angiogenic growth factor therapy. In addition, the newly developed variation of MR perfusion imaging that relies on generation of space-time maps proved capable of detecting changes in coronary perfusion in a pig ameroid model and proved capable of detecting improved regional myocardial perfusion in patients treated with epicardially administered sustained release FGF-2.

A fundamental question pertaining to IC delivery is how a drug with a relatively short plasma half-life can promote a relatively long-term process such as new collateral formation. One possible explanation is that first-pass extraction at the desired site of action is the primary determinant of FGF-2 biological effect. Although such extraction certainly occurs, animal studies demonstrated that <1% of $^{125}$I-FGF-2 administered using the intracoronary route is deposited in the myocardium at 1 h and much less remains at 24 h. Although there is enhanced first-pass FGF-2 uptake in ischemic compared with normal myocardium, presumably due to increased expression of cellular heparin sulfates and FGF receptor-1, myocardial levels fall to very low levels at 24 h in both normal and ischemic regions of the heart. One speculative explanation is that this transient accumulation of FGF-2 in the ischemic myocardium sets in motion a self-amplifying cascade that includes the influx and endothelial adhesion of monocytes/macrophages and stimulation of expression of VEGF and other angiogenic cytokines, which may lead to prolonged and sustained action.

Safety Assessment. The safety of intracoronary rFGF-2 was assessed through clinical observations, electrocardiography, hemodynamic monitoring, hematologic and serum chemistry profiles, development of anti-rFGF-2 antibodies, detailed ophthalmological exams with fundus photography and assessment of renal function by determination of creatinine clearance and proteinuria using 24-h urine collection. Dose-limiting toxicity was predefined as a persistent (>10 min) drop in systolic blood pressure by >50 mm Hg, change in heart rate to >120/min or to <50/min, new clinically significant arrhythmia, new ischemic symptoms or ECG changes, new congestive heart failure, deterioration in renal function or any other serious adverse events.

Clinical follow-up and safety assessment. Clinical follow-up of at least six months was obtained on all patients. A total of 30 serious adverse events were reported in 22 patients. There was no apparent relationship between increasing dose of rFGF-2 and serious adverse events.

Four patients died. Two deaths were sudden and occurred 22 days (0.65 g/kg dose, EF 30%) and 114 days (48 g/kg dose, EF 22%) after rFGF-2 infusion. One death was due to complications of cardiac transplantation and one death was due to complications of large-cell lymphoma. Both instances of sudden death occurred in patients with reduced left ventricular function (22% and 30%). Although sudden death may be part of the natural history of their disease, potential partial revascularization in these patients may have induced ventricular tachyarrhythmias. The diagnosis of large-cell non-Hodgkin's lymphoma 10 days after rFGF-2 infusion most likely reflected the presence of disease that antedated IC rFGF-2 administration. Nevertheless, it is possible that rFGF-2 may have exacerbated the lymphoma course.

One patient (2 g/kg) died 72 days after rFGF-2 infusion from complications of cardiac transplantation after sustaining several myocardial infarctions beginning four days after drug infusion. One patient with preexisting lymphadenopathy (6 g/kg) died at 62 days from septic complications of large-cell lymphoma, which was diagnosed at 10 days after dosing. In retrospect, the lymphoma most likely predated rFGF-2 infusion. One additional patient was diagnosed with metastatic adenocarcinoma to the liver at day 431.

Four patients had non-Q-wave myocardial infarctions at days 5 (2 g/kg dose group), 68 (6 g/kg), 132 (0.33 g/kg) and 146 (48 g/kg). Four patients had revascularization procedures (CABC and aortic value replacement in one patient at day 68 [6 g/kg] and PTCA in three patients at day 100 (0.33 g/kg], 290 [24 g/kg], and 223 [48 g/kg]). One patient developed atrial fibrillation at day 37. The most commonly reported (>10% of patients) adverse events were asthenia (19%), hypotension (15%), dyspnea (13%), insomnia (13%), angina (12%) and palpitations (12%). Of these asthenia, hypotension, insomnia, and dyspnea were more common at higher doses. No patients withdrew from the study because of adverse events. Transient leukocytosis was observed in half the patients at $\geq$24 g/kg. Fluctuations in renal function occurred but were transient and not dose related. Proteinuria (>250 mg/24 h) occurred in four patients (7.8%). Ophthalmological exams with fundus photography at baseline and day 57 were available for 45 patients; seven patients lacked wither baseline or 57-day assessments. Forty patients (89%) showed no change from baseline, two patients improved by two ETDRS grades and three patients worsened by two grades (0.65, 2.0 and 36.0 g/kg groups).

Safety and Tolerability of RFGF-2 Administration. The ability to administer fairly high does of rFGF-2 (up to 36 g/kg IC) without significant hemodynamic effects is somewhat surprising given prior reports of severe FGF-2-induced hypotension and the known capacity of this cytokine to stimulate NO release and induce arteriolar vasodilation. Hypotension was dose-related and dose limiting, but was rapidly correctable by IV fluids. This finding is in sharp contrast to clinical experience with another NO-releasing growth factor, VeGF-$A_{165}$, where profound hypotension limits systemic administration. This difference in part may be attributable to careful hemodynamic monitoring in these patients and a requirement for adequate pressure (>12 mm Hg) before initiation of rFGF-2 infusion.

Preclinical studies as well as limited clinical experience to date suggested that renal insufficiency due to membranous nephropathy accompanied by proteinuria may be the most significant long-term side effect of FGF-2 administration. In this small trial, only four instances of proteinuria were observed. In should be noted, however, that all patients studied had normal renal function at baseline.

Additional-serious side effects included the occurrence of non-Q-wave myocardial infarction in four patients, raising the possibility that FGF-2 may have promoted growth, or destabilization of coronary plaque owing to its broad-spectrum mitogenicity and chemotactic activity. The latter possibility may be particularly relevant given the ability of FGFs to induce angiogenesis in vasa vasorum and the association between plaque angiogenesis and its growth and stability. Although these concerns are certainly worrisome, in the absence of a control group casual relationships cannot be confirmed or discounted.

Statistical methods. Data are pooled for all dose groups. Baseline characteristics and acute hemodynamic parameters are expressed as mean±standard deviation. Efficacy variables were analyzed using a linear mixed effects model with an unstructured covariance assumption for the repeated measurements, fit using the restricted maximum likelihood method. Model-based estimates of the means±standard errors (SEM) are presented. An overall F-test for equality across all time points was conducted first. If this initial test was statistically significant, pairwise t tests to compare baseline with each on-study time point were performed at the nominal a-level. All reported p-values are two-sided, and a p-value<0.05 was considered statistically significant.

Magnetic resonance (MR) imaging. Magnetic resonance (MR) imaging was performed at baseline and days 29, 57 and 180 in the body coil of a 1.5 T whole-body Siemens Vision or Philips NT system. Functional imaging was performed during breath-hold using shared-center FLASH or multishot echoplanar imaging in each of the three mutually perpendicular standard views, producing 16–24 sequential image frames each, collected over approximately 12 heartbeats to measure regional wall systolic thickening. MR blood arrival imaging was assessed as previously described. A series of four inversion recovery images was obtained with the inversion time (TI) adjusted to minimize signal intensity from myocardium. Using the best TI for nulling myocardial signal, a series of concurrent parallel images were acquired in diastole during breathhold, at baseline and after the bolus injection of contrast media (0.05 mmol/kg gadodiamide). Measurement of the timing of half-maximum signal arriving in the different parts of the myocardium demonstrated the existence of several distinct regions, including normal myocardium and areas exhibiting delayed contrast arrival (ischemic zones). For each scan, a pace-time map demonstrating distribution of contrast signal density over the left ventricular wall as a function of time was created. The extent of the territory demonstrating delayed arrival of contrast, defined as >1-s delay of contrast density reaching its 50% maximum value reflecting the most severely hypoperfused part of the myocardium, was then calculated and expressed ads percent of the total left ventricular myocardial area. MR analysis was performed by a core lab blinded to rFGF-2 dose assignment and to study sequence.

Quality of life assessment. There were significant improvements in all five scales of the Seattle Angina Questionnaire at days 57 and 180, as compared with baseline. In particular, angina frequency score increased (denoting improvement) from 39.8±3.8 at baseline to 68.8±4.0 (p<0.001) at day 57 and 64.7±4.5 at day 180 (p<0.001), overall p<0.001. Exertional capacity score increased from 49.2±2.8 at baseline to 64.5±3.1 at day 57 (p<0.001) and 73.0±3.8 at day 180 (p<0.001), overall p<0.001.

Exercise treadmill testing. A subset of patients with matching baseline and follow-up exercise treadmill protocols was selected for analysis. Among this group, the mean exercise time improved from 510±24 s at baseline (n=35) to 561±26 s at day 29 (n=28; p=0.023), 609±26 s at day 57 (n=31; p<0.001), and 633±24 s at day 180 (n=23; p<0.001).

Left ventricular function assessment. Magnetic resonance imaging was performed in 51 patients at baseline and was repeated at days 29 (n=47), 57 (n=45) and 180 (n=31) to assess resting left ventricular ejection fraction, regional wall motion, and myocardial contrast arrival. There was a small improvement in overall left ventricular ejection fraction over the course of the study (baseline 51.4±1.7%, day 29: 54.2±1.7% [p=0.02], day 57: 55.2±1.9% {p=0.003], day 180: 57.2±1.7% [p<0.001], overall p=0.002). The hypoperfused target area was selected for resting regional left ventricular wall motion analysis. Systolic thickening of this area (target wall) and normal wall were measured using a semiautomated quantification algorithm of short-axis MR images. Resting normal wall systolic thickening was 46.1±1.6% at baseline and did not change significantly throughout the study duration (p=0.16). Resting target wall thickening was significantly lower than normal wall thickening at baseline (34.0±1.7% vs. 46.1±1.6%, p<0.001). Target wall thickening significantly improved at days 29, 57, and 180 as compared to baseline [baseline: 34±1.7%, day 29: 38.7±1.9% (p=0.006), day 57: 41.4±1.9% (p<0.001), and day 180: 42.0±2.3% (p<0.001), overall p=0.001].

Myocardial perfusion assessment. Myocardial perfusion was assessed using MR imaging. The mean size of the delayed contrast arrival zone was 15.4±0.8% of the left ventricle at baseline and was similar to the global left ventricular extent of ischemia determined by nuclear perfusion imaging (17.3±1.8%). The size of the myocardial area demonstrating delayed contrast arrival was significantly reduced from baseline (15.4±0.8%) at day 29 (9.0±0.6%, p<0.001), day 57 (5.6±0.7%, p<0.001) and day 180 (4.9±0.8%, p<0.001), overall p<0.001.

There was no correlation between the dose and the various efficacy parameters studied.

Example 2

Safety and Efficacy of a Single Intrapericardial Injection of FGF-2 In a Porcine Model of Chronic Myocardial Ischemia.

Chronic Myocardial Ischemia Model. Yorkshire pigs of either sex weighing 15 to 18 kg (5–6 weeks old) were anesthetized with intramuscular (i.m.) ketamine (10 mg/kg) and haloethane by inhalation. A right popliteal cut-down was performed and a 4 French arterial catheter was inserted for blood sampling and pressure monitoring. Left thoracotomy was performed through the 4th intercostal space. The pericardium was opened, and an ameroid constrictor of 2.5 mm i.d. (matched to the diameter of the artery) was placed around the left circumflex coronary artery (LCX). The pericardium was closed using 6-0 Prolene suture, (J&J Ethicon, Cincinnati, Ohio) and the chest was closed. A single dose of i.v. cefazolin (70 mg/kg) was given, and i.m. narcotic analgesics were administered as needed. Animals then were allowed to recover for 3 weeks (time sufficient for ameroid closure) before growth factor delivery. The treatment of animals was based on the National Institutes of Health guidelines, and the protocol was approved by the Institutional Animal Care and Utilization Committee of the Beth Israel Deaconess Medical Center.

Growth Factor Delivery. Three weeks after ameroid placement, animals were anesthetized with i.m. ketamine (10 mg/kg) and isoflurane by inhalation. A right femoral cut-down was performed and an 8 French arterial sheath was inserted for blood sampling, pressure monitoring, and left heart catheterization. Coronary angiography was then performed in multiple views using a 7 French JR4 diagnostic catheter (Cordis, Miami, Fla.) to confirm LCX occlusion and to assess the extent of collateral circulation in the LCX distribution ("collateral index"). After LCX occlusion was documented, percutaneous subxyphoid pericardial access was undertaken. With the animals in the supine position, the epigastric area was prepped and draped. An epidural introducer needle (Tuohy-17) was advanced gently under fluoroscopic guidance with a continuous positive pressure of 20 to 30 mm Hg. Entry into the pericardial space was confirmed by the injection of 1 ml of diluted contrast. A soft floppy-tipped guidewire was then advanced into the pericardial space and the needle was exchanged for a 4 French infusion catheter.

The animals were randomized to one of five treatment groups:
1. Control: intrapericardial saline (n=10).
2. Heparin: intrapericardial heparin (3 mg, n=9).
3. FGF-2 30 µg: intrapericardial FGF-2 (30 µg)+3 mg of heparin (n=10).
4. FGF-2 200 µg: intrapericardial FGF-2 (200 µg)+3 mg of heparin (n=10).
5. FGF-2 2 mg: intrapericardial FGF-2 (2 mg)+3 mg of heparin (n=10).

The infusate was diluted to 10 ml with saline and infused over 5 min with continuous electrocardiographic and pressure monitoring. The catheter was withdrawn, and a set of colored microspheres (blue) was injected into the left atrium to obtain baseline (pretreatment) myocardial blood flow. Finally, a magnetic resonance study was carried out to obtain quantitative measures of global and regional left ventricular function [ejection fraction (EF) and radial wall motion] and assessment of perfusion using myocardial contrast density mapping. The animals then were allowed to recover for 4 weeks.

Final Study. Four weeks after intrapericardial agent administration, all animals underwent final evaluation. Pigs were anesthetized with i.m. ketamine (10 mg/kg) and isoflurane by inhalation. A left femoral cut-down was performed and an 8 French arterial sheath was inserted for blood sampling, pressure monitoring, and left heart catheterization. Coronary angiography was performed again in multiple views. A second magnetic resonance study was carried out for global and regional left ventricular function and myocardial perfusion. Myocardial blood flow was determined using colored microspheres at rest (yellow) and after maximal coronary vasodilation with i.v. adenosine (white). Animals then were euthanized under anesthesia and the heart was obtained for additional analysis. In addition, a detailed macroscopic and histologic postmortem examination was carried out on three animals in each group.

A total of 56 animals survived ameroid placement around the LCX coronary artery with resultant total LCX occlusion at 3 weeks. Seven animals died after being randomized to a treatment group. Six of these seven animals died within 72 h of intrapericardial agent delivery. Of the seven animals deaths, two animals died of hypoxemia (one control animal and one FGF-2 30 µg animal) due to failure of mechanical ventilation before growth factor delivery, four animals died during MRI (three animals died before growth factor delivery and one after pericardial access and delivery, with two animals randomized to the 200 µg FGF-2 group and two animals in the control group), and one animal died of unknown cause 26 days after growth factor delivery (heparin group). The remaining 49 animals were randomized to each of five treatment groups with 10 animals in each of the FGF-2 and saline control groups and 9 animals in the heparin group. There were no significant hemodynamic effects of intrapericardial FGF-2 administration at any dose; no changes in blood pressure, heart rate, or left atrial pressure were observed with drug administration.

Angiographic Analysis. Coronary angiography was performed in multiple views (right anterior oblique, anteroposterior, and left anterior oblique views for the left coronary artery; right anterior oblique and left anterior oblique for the right coronary artery). Evaluation of angiographic collateral density was performed by two independent angiographers blinded to treatment assignment. Differences in interpretations were resolved by a third angiographer. The collateral index was assessed for left-to-left and right-to-left collaterals using a 4-point scale (0, no visible collateral vessels; 1, faint filling of side branches of the main epicardial vessel without filling the main vessel; 2, partial filling of the main epicardial vessel; and 3, complete filling of the main vessel).

Coronary Angiography Baseline right and left coronary angiography was available on all 49 animals and final angiography was available on 47 animals. Left-to-left collaterals and right-to-left collaterals were measured (collateral index). The extent of left-to-left collaterals pre-(3 weeks after ameroid placement) and post-treatment (7 weeks after ameroid placement) in all groups shows a significant improvement over baseline in the collateral index of all three FGF-2 treatment groups (30 µg, 200 µg, and 2 mg) with no significant improvement noted in control or heparin-treated animals. Only animals in the FGF-2 2 mg group displayed a trend toward improvement in right-to-left collateral index (collateral index increased by 0.67±0.87, P=0.06).

Myocardial Blood Flow. Colored microspheres (15±0.1 µm diameter; Triton Technology Inc., San Diego, Calif.) were used to determine coronary blood flow before treatment initiation (blue) and at the time of final study (yellow and white). For determination of coronary flow at 3 and 7 weeks after ameroid placement, an angiographic JR4 catheter was advanced into the left ventricle and manipulated to engage the left atrium outflow by slow counterclockwise rotation of the catheter; catheter position was verified by contrast injection into the left atrium. In addition, mean left atrial pressure was recorded. A set of microspheres ($6 \times 10^6$) was diluted in 10 ml of saline and injected into the left atrium over 30 s. Reference blood samples were withdrawn by using a syringe pump at a constant rate of 5 ml/min through the femoral artery. At the time of final study, coronary flow was measured at rest and after maximal vasodilation (achieved with the injection of i.v. adenosine, 1.25 mg/kg). After study completion, the heart was excised and regional myocardial blood flow was determined. The heart was excised and a 1-cm midtransverse slice was sectioned and cut into eight segments. The tissue samples and the reference blood samples were digested in an 8 M KOH/2% Tween 80 solution and microspheres were collected using a vacuum filter. Dyes from microspheres were extracted using dimethyl formamide. Samples were then analyzed in a spectrophotometer (HP 8452 A; Hewlett Packard, Palo Alto, Calif.).

Regional blood flow was calculated from optical absorbance (AU) measurements corrected by tissue weight as follows:

$$\text{Flow to sample (mL/min/g)} = \frac{(AU/\text{sample})(\text{reference withdrawal rate})/\text{wt.}}{(AU/\text{reference sample})}$$

To evaluate further the angiogenic potential of intrapericardial FGF-2 in chronic myocardial ischemia, regional myocardial blood flow was measured at different time points using colored microspheres. Three weeks after implantation of ameroid occluders, at the time of intrapericardial drug delivery, resting myocardial blood flow in the LCX territory was similar in all treatment groups [baseline coronary flow (ml/min/g): 1.00±0.31 in controls and 0.97±0.23 in heparin-treated animals versus 0.92±0.08 in the 30 μg FGF-2 group, 0.99±0.15 in the 200 μg FGF-2 group, and 1.10±0.14 in the 2 mg FGF-2 group, P=0.94] and was significantly lower than flow in the LAD territory (LCX flow: 1.00±0.35 ml/min/g versus LAD flow: 1.43±0.43 ml/min/g, P<0.0001). Four weeks after intrapericardial drug delivery, LCX flow was significantly higher in FGF-2-treated animals than in controls and heparin-treated animals (ANOVA P=0.002). At the time of the final study, coronary flow (ml/min/g) was 1.05±0.21 in controls (P=0.7 compared with baseline) and 1.09±0.13 in the heparin group (P=0.19 compared with baseline and P=0.6 compared with controls) versus 1.31±0.12 in the 30 μg FGF-2 group (P=0.0001 compared with baseline and P=0.004 compared with controls), 1.25±0.15 in the 200 μg FGF-2 group (P=0.002 compared with baseline and P=0.03 compared with controls), and 1.32±0.16 in the 2 mg FGF-2 group (P=0.004 compared with baseline and P=0.005 compared with controls).

MRI. MRI was performed on all animals at the time of treatment initiation and at the time of final study. MRI was carried out in the body coil of a 1.5 Tesla whole body Siemens Vision system (Iselin, N.J.) as previously described.

The following measurements were performed:
a. Determination of resting left ventricular EF (%).
b. Analysis of regional wall motion using percentage of wall thickening.
c. Determination of the extent of coronary perfusion in the LCX collateral-dependent territory compared with normal myocardium by measuring gadodiamide-enhanced signal intensity in different parts of the left ventricular wall and generating a space-time map of myocardial perfusion). The space-time maps allow the measurement of the extent of the ischemic zone.

MRI was available on 44 animals (8 in the control group; 9 in the heparin group; and 9 in each of the 30 μg, 200 μg, and 2 mg FGF-2 groups). In five animals, MRI was not performed due to temporary technical problems with the MRI system at the time of the final study. The porcine ameroid occlusion model is associated with the development of small areas of left ventricular myocardial necrosis in most animals.

Global Left Ventricular Function. To assess the functional significance of FGF-2-mediated improvement in myocardial blood flow, MRI was used to assess global and regional left ventricular function in all study animals. There were no significant differences in global left ventricular function among the five groups (EF was 44.1±6.4% in controls and 44.2±6.8% in heparin-treated animals versus 47.07±2.68 in the 30 μg FGF-2 group, 45.52±3.41 in the 200 mg FGF-2 group, and 47.98±3.14 in the 2 mg FGF-2 group; ANOVA, P=0.35).

Regional Left Ventricular Function. Measurement of regional wall thickening in the LAD (normal territory) and LCX (ischemic) territories was used to assess regional left ventricular function (FIG. 2). LAD (normal) wall thickening was similar in all groups (ANOVA, P=0.86). FGF-2-treated animals had improved regional wall thickening in the LCX (ischemic) territory compared with controls and heparin-treated animals [FIG. 2; LCX wall thickening (%): controls, 33.58±9.91; heparin, 32.64±13.45 (P=0.87 compared with controls); FGF-2 30 μg, 42.12±6.43 (P=0.05 compared with controls); FGF-2 200 μg, 43.23±6.41 (P=0.03 compared with controls); and FGF-2 2 mg, 47.14±3.64 (P=0.002 compared with controls); ANOVA, P=0.003]. Linear regression (assuming heparin results in no significant FGF-2 release) revealed a dose-dependent improvement in LCX wall thickening in the FGF-2-treated animals (y=37.6+0.005x, P=0.007)

Figure 3:
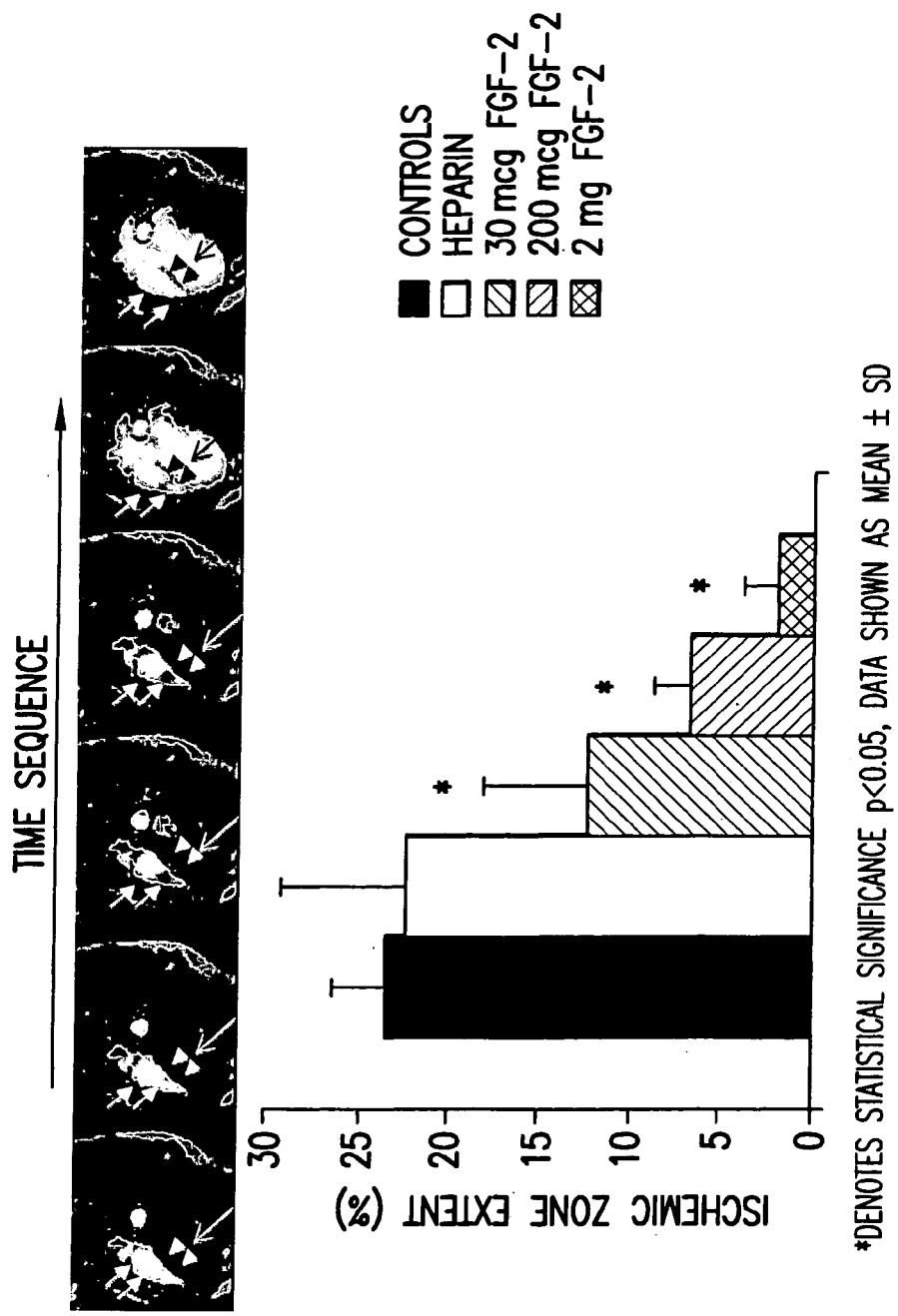

Myocardial Perfusion. First-pass inversion-recovery turboFLASH MRI was used to generate a space-time map of myocardial perfusion (FIG. 3 top). Three distinct zones are observed that are characterized by either prompt signal appearance, failure of the signal to increase in intensity (infarction), or delayed signal appearance (delayed contrast arrival or ischemic zone). On the basis of contrast density data, a two-dimensional map of contrast intensity versus time was generated and was used to measure the size of the myocardial segments showing impaired (delayed) contrast arrival. FIG. 3 (bottom) depicts the extent of the ischemic zone of contrast in the five groups. FGF-2 induced a dose-dependent reduction in the extent of the ischemic zone, indicating achievement of better myocardial perfusion in the FGF-2 treatment groups [FIG. 3 bottom; ischemic zone (% of left ventricle): controls, 23.54±2.84; heparin, 22.41±6.85 (P=0.66 compared with controls); FGF-2 30 μg, 12.27±5.82 (P=0.0001 compared with controls); FGF-2 200 μg, 6.63±1.97 (P<0.0001 compared with controls); and FGF-2 2 mg, 2.02±1.83 (P<0.0001 compared with controls); ANOVA, P<0.0001; linear regression y=16.7−0.008x, P<0.0001].

Histopathologic Analysis and Toxicology. Complete autopsies were performed on 15 animals (3 animals in each group). Tissues obtained from the liver, lung, kidney, spleen, eye, bone marrow, and stomach were formalin-fixed and paraffin-embedded. Sections (5 μm) were obtained from all tissue samples, stained with hematoxylin/eosin, and examined microscopically. In addition, tissue samples were obtained from pericardium, epicardial coronary artery, and myocardium in the left anterior descending coronary artery (LAD) distribution (normal) and LCX distribution (ischemic). Sections were stained with hematoxylin/eosin as well as by the Verhoeff-Van Gieson method for collagen and elastin. Complete serum chemistry and hematology studies were performed at 3 and 7 weeks in all animals.

There were no treatment-related macroscopic or microscopic findings in any of the organs examined. One animal had a single kidney present. There was focal to diffuse minimal thickening of the pericardium in all FGF-2 treatment groups, which was due to a slight increase in connective tissue (fibrosis). There were minimal to mild chronic inflammatory cell infiltrates accompanied by focal or multifocal mineralization in all FGF-2 treatment groups. Increased vascularity was noted in the pericardium of two of three animals examined in the 200 μg FGF-2 group and one of three animals examined in the 2 mg FGF-2 group, but was not observed in the control, heparin, or 30 μg FGF-2 groups (FIG. 4B). In addition, the LAD and LCX in these animals were examined and they showed no evidence of intimal hyperplasia.

Finally, there was an increase in vascularity of the epicardium and myocardium in all animals from the 30 μg, 200 μg, and 2 mg FGF-2 groups, but not in controls or heparin-treated animals. Sections from the LCX but not the LAD distribution in all FGF-2 treatment groups showed an increase in the number of capillaries. Many of these small blood vessels were lined by endothelial cells that had large hyperchromatic nuclei, suggestive of new vascular in-growth (FIG. 4A). FGF-2 treatment did not result in any significant abnormalities in serum chemistries, hematology, and coagulation studies.

Example 3

Nonmitogenic Effects of Administration of FGF-2 in Acute Myocardial Ischemia and Reperfusion in a Murine Model To determine whether nonmitogenic effects of FGF-2 could be beneficial to the heart during acute myocardial ischemia and reperfusion, FGF-2 was administered in a murine model of myocardial stunning. The advantages of this mouse model are well-defined markers of ischemia-reperfusion injury, including ischemic contracture, alteration in calcium homeostasis, and prolonged ventricular dysfunction, occurring within a time window too short to activate the mitogenic properties of FGF-2. Transgenic mouse hearts deficient in the expression of the inducible isoform of NOS (NOS2−/−) were used to further investigate the coupling of FGF-2 and NO during acute myocardial ischemia and reperfusion.

Stunning Myocardial stunning is the phenomenon whereby an ischemic insult interferes with normal cardiac function, cellular processes, and ultrastructure for prolonged periods. Numerous mechanisms of myocardial stunning have been proposed, the most probable of which include generation of oxygen-derived free radicals, metabolic impairment, and calcium overload. Recently, a number of pharmacological agents and physiological manipulations have been shown to induce early or late ischemic preconditioning, a state characterized by reduced susceptibility to postischemic decline in myocardial function. In particular, FGF-2 has been demonstrated to improve myocardial function in the setting of acute myocardial ischemia both in vivo and in isolated rat heart studies. The well-known angiogenic effects of FGF-2, however, occur too gradually to be relevant in such settings. The purpose of this study, therefore, was to study the potential role of NO release in FGF-2-mediated cardioprotection and to define the NOS isoform responsible for FGF-2-induced NO release.

Fifteen minutes of global ischemia followed by twenty minutes of reperfusion resulted in prolonged ventricular dysfunction characterized by reduced levels of LVP generation as well as significant decreases in $dP/dt_{max}$ and $dP/dt_{min}$. Pretreatment with rFGF-2 significantly improved the extent of recovery of LVP compared with control (untreated) hearts (83±5 vs. 61±6%) and equally significant preservation of $dP/dt_{max}$ and $dP/dt_{min}$ (86±3 vs. 65±6% and 85±5 vs. 60±5%, respectively. Stunning in hearts perfused with either NOS inhibitor by itself was not different from that in control hearts. Functional recovery of LVP in untreated control hearts (61±6%) was not significantly different from that in hearts perfused with either L-NAME alone (59±9%) or L-NIL alone (57±6%). Depression of $dP/dt_{max}$ and $dP/dt_{min}$ (65±6 and 60±5%, respectively) in untreated hearts was similar to that in hearts perfused with L-NAME alone (60±9 and 55±8%, respectively) and hearts perfused with L-NIL alone (57±9 and 67±4%, respectively).

Unlike initial pretreatment with rFGF-2, addition of the growth factor to the coronary perfusate after the onset of ischemia, immediately before reperfusion, did not improve LV function 20 min after reperfusion (LVP 60±4%, $dP/dt_{max}$ 62±4%, and $dP/dt_{min}$ 58±4%, all P=NS vs. control). As in the case of acute ischemic changes, pretreatment with either L-NAME or L-NIL led to a complete inhibition of rFGF-2 effects (FIGS. 2 and 3).

Isolated Heart Preparation Hearts were excised from adult C57/BL6 mice of either sex that had been anesthetized and heparinized (500 U/100 g body wt). The aorta was slipped over a 20-gauge blunt-tipped stainless steel needle through which oxygenated (95% $O_2$-5% $CO_2$) Krebs-Henseleit (KH) buffer (in mM: 118.0 NaCl, 4.7 KCl, 1.2 $KH_2PO_4$, 1.5 $CaCl_2$, 1.2 $MgCl_2$, 23.0 $NaHCO_3$, 10.0 dextrose, and 0.3 EDTA, pH 7.4) was pumped at a rate of ~3 ml/min. An intraventricular balloon catheter system specially designed for the mouse heart was passed through the mitral annulus into the left ventricle, and the distal end of the balloon catheter was connected to a Statham P23b (Gould, Cleveland, Ohio) transducer to record intraventricular pressure. Left ventricular (LV) pressure recordings were analyzed with regard to LV developed pressure (LVP), LV end-diastolic pressure, peak rate of pressure development ($dP/dt_{max}$), time to 90% pressure decline, and peak rate of pressure decline ($dP/dt_{min}$).

Ischemia and reperfusion. The hearts were subjected to no-flow ischemia for 15 min. The organ bath was evacuated of its oxygenated solution and refilled with nitrogen-saturated perfusate. Pacing was maintained during ischemia. LV pressure was monitored throughout ischemia and reperfusion. All hearts ceased to contract within 3 min. The time for LVP to fall to 10% of baseline ($T_{LVP10}$) was measured to quantify differences in LV function during early ischemia. Mean ischemic $Ca_i^{2+}$ was calculated as the mean $Ca_i^{2+}$ recorded from the 2nd through the 14th minute of ischemia. Contracture was defined as an abrupt and sustained rise in intraventricular pressure above 4 mmHg. Contracture time was measured as the time from the onset of ischemia to the onset of contracture. At the end of 15 min of ischemia, the nitrogen-saturated bath was replaced by the original bath maintained at 30° C. Flow was recommenced. Mean $Ca_i^{2+}$ during early reflow was calculated as the mean of the peaks of $Ca_i^{2+}$ recorded during the 1st minute of reperfusion. After 20 min of reperfusion, $Ca_i^{2+}$ and functional parameters were again measured.

Drugs. Recombinant bovine FGF-2 (rFGF-2) was obtained from Chiron (Sunnyvale, Calif.). $N^G$-nitro-L-arginine methyl ester (L-NAME), an inhibitor of NOS, was obtained from RBI (Natick, Mass.). L-$N^6$-(1-iminoethyl) lysine (L-NIL), a selective inhibitor of NOS2, was obtained from Sigma (St. Louis, Mo.). All studies were conducted at 30° C., and hearts were paced at 6 Hz to minimize consumption of aequorin. After a 15-min equilibrium period, baseline conditions were recorded. Subsequently, hearts were divided into the following perfusion groups: perfusion with KH for 40 min (control, n=10), perfusion with KH for 20 min followed by perfusion with KH plus 1 µg/ml rFGF-2 for 20 min (rFGF-2, n=10), perfusion with KH plus 400 µM L-NAME for 20 min followed by perfusion with KH plus 400 µM L-NAME plus 1 µg/ml rFGF-2 for 20 min (L-NAME+rFGF-2, n=6), and perfusion with KH plus 400 µM L-NIL for 20 min followed by perfusion with KH plus 400 µM L-NIL plus 1 µg/ml rFGF-2 for 20 min (L-NIL+rFGF-2, n=5). To test the effect of perfusion with the NOS inhibitors in the absence of rFGF-2, the following two additional perfusion groups were studied: perfusion with KH for 20 min followed by perfusion with KH plus 400 µM L-NAME for 20 min (L-NAME, n=5), and perfusion with KH for 20 min followed by perfusion with KH plus 400 µM L-NIL for 20 min (L-NIL, n=5).

Measurement of Intracellular $Ca^{2+}$ In hearts in which intracellular $Ca^{2+}$ ($Ca_i^{2+}$) was estimated, aequorin was injected into the apex of the heart. Briefly, after the perfusate was modified to contain 0.5 mM $CaCl_2$, 0.6 mM $MgCl_2$, and 20 mM dextrose, 1–3 µl of aequorin were injected with a glass micropipette into a localized region of 2 mm² at the apex of the heart. The heart was positioned in an organ bath such that the aequorin-loaded region was ~2 mm from the bottom of the bath. The $Ca^{2+}$ and $Mg^{2+}$ concentrations of the perfusate were increased to 2.5 mM $Ca^{2+}$ and 1.2 mM $Mg^{2+}$ in a stepwise fashion over a period of 40 min. The entire isolated heart preparation was positioned in a light-tight box for collection of the aequorin light signal. Aequorin luminescence was detected by a photomultiplier tube and recorded as anodal current. For estimation of $Ca_i^{2+}$, Triton X-100 was injected into the coronary perfusate to quickly permeabilize the myocardial cell membranes and expose the remaining active aequorin to saturating $Ca^{2+}$. This resulted in a burst of light, the integral of which approximated the maximum light ($L_{max}$) against which light signals of interest (L) provided the fractional luminescence ($L/L_{max}$). $L/L_{max}$ was referred to a calibration equation to estimate $Ca_i^{2+}$.

Myocardial Calcium Homeostasis. Changes in myocardial $Ca_i^{2+}$ are thought to play an important role in ischemia-induced myocardial dysfunction. Therefore, additional experiments were carried out to assess the effect of rFGF-2 administration on myocardial ionized calcium levels. Myocardial $Ca_i^{2+}$ measured at baseline was not different between NOS2+/+ and NOS2–/– hearts, and pretreatment with rFGF-2 had no effect on these levels. Interruption of coronary flow produced abrupt alterations in $Ca_i^{2+}$ in all hearts, with a gradual rise in diastolic and peak $Ca_i^{2+}$ as ischemia progressed. Mean ischemic $Ca_i^{2+}$, $Ca_i^{2+}$ averaged from the 2nd through the 14th minute of ischemia, was not affected by rFGF-2 pretreatment and was the same in NOS2+/+ and NOS2–/– hearts. Restoration of coronary flow was followed by a marked increase in myocardial $Ca_i^{2+}$. Neither the extent of this increase nor peak $Ca^{2+}$ levels was affected by rFGF-2 administration in NOS2+/+ or NOS2–/– hearts.

Measurement of NO Additional NOS2+/+ (n=5) and NOS2–/– hearts (n=5) were used to measure NO concentration in the coronary effluent using an amperometric sensor (ISO-NO, World Precision Instrument, Sarasota, Fla.). Briefly, after 20 min of perfusion with either vehicle or 1 µg/ml rFGF-2, the electrode was positioned in the effluent to measure the amount of NO released from the coronary sinus. Electrode calibration was performed before each experiment with NO generated from the reaction of S-nitroso-N-acetyl-penicillamine (Sigma) with cupric sulfate (Sigma) and acidic solution.

Quantification of NOS Gene Expression To determine NOS2 and NOS3 mRNA levels in FGF-2-treated compared with control hearts, 30 cycles of RT-PCR were performed on equal amounts of total RNA from six control and six rFGF-2-treated hearts using primers corresponding to human NOS3 and NOS2 sequences. For NOS3, primers were as follows: 5' (sense), 5'-CAGTGTCCAACATGCT-GCTGGAAATTG-3' (bases 1,050–1,076); antisense, 5'-TAAAGGTCTTCTTGGTGATGCC-3' (bases 1,511–1,535). For NOS2, primers were as follows: 5' (sense), 5'-GCCTCGCTCTGGAAAGA-3' (bases 1,425–1,441); antisense, 5'-TCCATGCAGACAACCTT-3' (bases 1,908–1,924). Glyceraldehyde-3-phosphate dehydrogenase (GAPDH) mRNA was amplified from the same amount of RNA at the same time to correct for variation between different samples. The PCR products, separated on 1% agarose gels, were scanned and quantitated using Image-Quant software (Molecular Dynamics).

For Northern analysis of NOS1 and NOS3 mRNA levels in hearts of NOS2–/– and wild-type mice, total RNA was prepared from freshly excised hearts, subjected to electrophoresis on 1% paraformaldehyde-agarose gel, transferred to the GeneScreen Plus membrane (Dupont), and probed with random-primed mouse NOS1 and NOS3 cDNA probes. GAPDH cDNA probe was used to control for loading. Quantification was achieved using Image-Quant software.

Role of NOS2 The studies suggested that the NOS2 isoform was the primary NOS isoform responsible for FGF-2-induced preservation of myocardial function in this model. To further corroborate these results, the same studies were repeated in hearts from NOS2–/– mice using their NOS2+/+ littermates as controls. As in the case of previous studies, ischemia in both NOS2+/+ and NOS2–/– hearts was characterized by an abrupt fall in LV pressure, a gradual onset of ischemic contracture, and prolonged ventricular dysfunction throughout 20 min of reperfusion. rFGF-2 pretreatment prolonged $T_{LVP10}$, reduced the onset of contracture, and improved LV recovery throughout reperfusion. However, in NOS2–/– hearts, rFGF-2 failed to provide any protective effects against global ischemia and stunning as measured by changes in LVP, $dP/dt_{max}$, and $dP/dt_{min}$ after 20 min of reperfusion.

Release of NO and FGF-2 Effects on NOS Gene Expression To directly demonstrate the role of rFGF-2-induced NO release, the concentration of NO in coronary effluent before and after rFGF-2 administration was measured. NO concentration increased significantly after perfusion with rFGF-2 compared with measurements after perfusion with vehicle (236±24 vs. 190±25 nM/g, P<0.05) in wild-type hearts. In contrast, perfusion with rFGF-2 did not increase NO concentration in NOS2–/– hearts compared with NO values measured after perfusion with vehicle (170±24 vs. 154±46 nM/g, P=NS). To assess whether rFGF-2 increased NO production by stimulating NOS enzyme or increasing its gene expression, we carried out RT-PCR analysis of NOS2 and NOS3 mRNA levels before and after 40 min of exposure to rFGF-2. No differences in either NOS2 or NOS3 levels were detected.

The "knockout" of the NOS2 gene may have affected expression of NOS1 or NOS3 genes in these mice. To evaluate this possibility, we performed Northern analysis of NOS1 and NOS3 gene expression in hearts from C57/BL6 NOS2+/+ and NOS2–/– mice. No significant changes in expression of either gene compared with that in control mice were detected.

Statistical Analysis Observations made before and after drug administration were compared using Student's two-tailed paired t-test. Observations made before and after the ischemia-reperfusion protocol within a group were compared using Student's two-tailed paired t-test. Between-group comparisons were made using analysis of variance. When an overall significance was observed, multiple comparisons were performed using the Bonferroni-modified t-test. A value of P<0.05 was considered significant. Data are expressed as means±SE.

Baseline Conditions and Effects of Ischemia Baseline parameters of cardiac function including myocardial $Ca_i^{2+}$ were similar at baseline in all groups and were not affected by administration of L-NAME, L-NIL (not shown), or rFGF-2. Interruption of coronary flow led to an abrupt fall in LV pressure in all hearts. This fall in LV pressure during early ischemia was significantly attenuated in hearts pretreated with rFGF-2 compared with control hearts. Pretreatment with rFGF-2 prolonged $T_{LVP10}$ (124±9 vs. 74±5 s, rFGF-2 vs. control, P<0.05) and significantly delayed the onset of contracture (893±7 vs. 819±36 s, rFGF-2 vs. control, P<0.01).

To explore the role of NO in mediation of this cardioprotective effect of FGF-2, L-NAME was used to inhibit all isoforms of NOS in the heart. Pretreatment with L-NAME completely blocked the cardioprotective effects of rFGF-2 during ischemia, significantly reducing $T_{LVP10}$ (79±2 vs. 124±9 s, L-NAME+rFGF-2 vs. rFGF-2, P<0.05) and accelerating the onset of ischemic contracture (674±24 vs. 893±7 s, L-NAME+rFGF-2 vs. rFGF-2, P<0.05). However, perfusion with L-NAME alone (in the absence of rFGF-2) did not affect either $T_{LVP10}$ [69±3 vs. 74±5 s, L-NAME vs. control, P=not significant (NS)] or the onset of ischemic contracture (820±24 vs. 819±36 s, L-NAME vs. control, P=NS).

To further define the type of NOS enzyme involved in this FGF-2 response, a NOS2-selective inhibitor, L-NIL, was used. Similarly to L-NAME, L-NIL fully inhibited the cardioprotective effects of rFGF-2, significantly reducing $T_{LVP10}$ (62±3 vs. 124±9 s, L-NIL+rFGF-2 vs. rFGF-2, P<0.05) and accelerating the onset of ischemic contracture (652±16 vs. 893±7 s, L-NIL+rFGF-2 vs. rFGF-2, P<0.05). Similarly to perfusion with L-NAME, perfusion with L-NIL alone, in the absence of rFGF-2, did not affect either $T_{LVP10}$ (67±6 vs. 74±5 s, L-NIL vs. control, P=NS) or the onset of ischemic contracture (740±39 vs. 819±36 s, L-NIL vs. control, P=NS).

Example 4

Efficacy of Intracoronary Versus Intravenous FGF-2 an a Porcine Model of Chronic Myocardial Ischemia A porcine ameroid model was chosen for preclinical testing of delivery strategies because of several unique aspects. First, the ameroid occluder results in consistent and gradual occlusion of the LCX, resulting in minimal myocardial necrosis, but reduced regional myocardial function, which is detectable with various noninvasive imaging modalities. Because an effect of estrogen on cardiac angiogenesis cannot be ruled out and synchronization of these studies with the menstrual cycle is logistically impossible, females were excluded from this study. In a similar model in dogs, daily intracoronary injections of FGF-2 also induced increased vascularity of ischemic myocardium. Although very encouraging, there are little data considering the efficacy of single intravascular administration of angiogenic growth factors.

MATERIALS AND METHODS Male Yorkshire pigs (n=57; Parsons, Hadley, Mass.) weighing 15 to 30 kg were used for this study. The chronic ischemia model consisted of three phases as previously described [4, 7]. In brief, for ameroid surgery and catheterization at 3 and 6 weeks, the animals were anesthetized with Ketamine 20 mg/kg IM and pentothal 10 mg/kg IV, intubated, mechanically ventilated, and further anesthetized with 1.5% to 2.5% isoflurane in room air. Postoperatively, all animals received antibiotics and analgesics for 48 hours. Animal care was performed according to the National Institutes of Health's *Guidelines for the Care and Use of Laboratory Animals*, and the protocol was approved by the Institutional Animal Care Committee.

A plastic ameroid (inner diameter, 2 to 2.5 mm; Research Instruments, Escondido, Calif.) was placed on the proximal left circumflex artery (LCX) or a major side branch, through a left lateral fourth intercostal thoracotomy. Three weeks (second phase, midstudy) later, right and left coronary catheterization was performed through a standard femoral cut-down after systemic anticoagulation with Heparin 100 U/kg. Intraarterial pressure and electrocardiogram were continuously recorded. Selective left and right angiography (General Electric, Waukesha, Wis.; contrast: Renografin; Squibb Diagnostics, Princeton, N.J.) confirmed complete occlusion of the LCX and allowed assessment of baseline flow and the presence of collaterals in the LCX territory, according to the Rentrop scoring system from 0 to 3:0=none; 1=filling of side branches of the LCX; 2=partial filling of the LCX main artery via collateral channels; 3=complete filling of the LCX. Angiographic analysis was blinded to treatment. For regional blood flow measurements, colored microspheres were injected into the left atrium (see below). Directly after this, function, perfusion, and collateral sensitive magnetic resonance imaging (MRI) was performed on all animals to quantify baseline regional cardiac function and perfusion before start of the treatment.

Pigs were then randomly assigned to one of the following treatments: 1) vehicle control; 2) 2 µg/kg rFGF-2 IV; 3) 6 µg/kg rFGF-2 IV; 4) 2 µg/kg rFGF-2 IC; 5) 6 µg/kg rFGF-2 IC. Five minutes before FGF-2 administrations, heparin (70 U/kg, IV) was given. Bovine recombinant FGF-2 (rFGF-2; Chiron Corporation, Emeryville, Calif.) was dissolved and diluted in vehicle consisting of 10 mmol/L sodium citrate, 10 mmol/L thioglycerol, 135 mmol/L sodium chloride, 100 mmol/L EDTA, pH 5.0. The intracoronary FGF-2 was equally divided and infused into the right coronary artery (RCA) and the proximal LCX using a 3F Cordis infusion catheter. Intravenous infusions were given through an ear vein. In short proximal LCX stumps, FGF-2 was delivered into the proximal part of the LAD. The vehicle control group consisted of animals that received intravenous vehicle (n=4) or intracoronary vehicle (n=4). Three weeks after therapy (third phase, final study), repeat selective angiograms were made and two sets of colored microspheres were injected into the left atrium, one before (rest) and one after injection of Adenosine 1.25 mg/kg IV (stress). Function and perfusion MRI was also repeated in all animals. Finally, animals were euthanized and the hearts were excised.

Fifty-seven animals received an ameroid constrictor and 13 animals died before initiation of treatment. Forty-four animals (control, n=10; FGF 2 µg/kg IV, n=9; FGF 6 µg/kg IV, n=9; FGF 2 µg/kg IC, n=8; and FGF 6 µg/kg IC, n=8) completed the entire study.

Regional blood flow For microspheres injection into the left atrium, a 7F JL4 catheter was retrogradely advanced across the aortic and mitral valve into the left atrium. The left atrial position of the catheter was confirmed by contrast injection and the presence of an atrial pressure waveform. At midstudy, and during the final study at rest and stress, $6\times10^6$ microspheres (Dye Trac; Triton Technologies, San Diego, Calif.) were injected according to a standard protocol Reference blood samples were drawn simultaneously. At the end of the study (final study), a mid papillary, 1-cm-thick cross section of left ventricle was taken and divided into eight radial segments. The segment in the LCX territory was further subdivided in an endocardial and epicardial piece. Tissue samples and reference blood samples were digested and the microspheres retrieved according to the manufacturers protocol. The samples were analyzed with a spectrophotometer (SU 600; Beckman, Fullerton, Calif.). From the optical density (OD) measurements, the myocardial flow was calculated as blood flow: (tissue sample X; mL/min/g) =[withdrawal rate (mL/min)/weight (tissue sample X; g)]×

[OD (tissue sample X)/OD (reference blood sample)], using the Excel worksheet and macros provided by the manufacturer.

Hemodynamic parameters Intravenous infusion caused a mild but significant decrease in blood pressure of 12.3±3.7 mm Hg (p=0.02) in the FGF 2 μg/kg IV group and 9.6±2.1 mm Hg (p=0.01) in the FGF 6 μg/kg IV group. After intracoronary infusion, the drop in blood pressure was significant only at 2 μg/kg with 10.0±2.2 mm Hg (p=0.04) and not at 6 μg/kg (6.1±4.9 mm Hg, p=0.25). In all groups, heart rate decreased mildly, ranging from 2 to 15 bpm, but was significant only in the FGF 2 μg/kg IV with 9±4 bpm (p=0.05) and 6 μg/kg IC group with 18±6 bpm (p=0.03).

Coronary angiography Seven follow-up angiograms, two in the control group, two in the FGF 2 μg/kg IV, one in the FGF 6 μg/kg IV, and two in the FGF 2 μg/kg IC group, were not available for analysis. Collateral index had improved significantly in the 6 μg/kg IV group and in both 2 and 6 μg/kg IC groups, whereas baseline collateral index was similar (p=0.119, Kruskal Wallis). For all groups pooled, collateral index resulted from left-to-left collaterals (either LAD to LCX or LCX to LCX, n=37; p<0.001, McNemar test) and not from right-to-left (p=1.0), suggesting a localized effect of intravascular drug delivery. However, changes were not significant in any subgroup.

Coronary blood flow. Baseline regional blood flow in the ischemic (LCX) and normal (LAD) territories was measured at rest and posttreatment (final study) at rest and stress (adenosine). Absolute ischemic flow (mL/min/g tissue) and the LCX/LAD flow ratio were determined. LAD flow at baseline, rest, and stress at the final study were similar in the five groups (ANOVA, p=0.363, p=0.418, and p=0.331, respectively). Rest LAD flow did not change significantly over time (ANOVA, p=0.266). In addition, LCX coronary blood flow at baseline (before FGF2 infusion) was similar in all five groups (ANOVA, p=0.36.1). At the final study at rest, absolute LCX flow and the LCX/LAD ratio did not change significantly. However, LCX flow at stress was significantly higher in the FGF 6 μg/kg IC group than in controls (ANOVA, p=0.039).

Myocardial MRI analysis. Arterial pulse-gated MRI was performed on anesthetized (1% to 2% isoflurane) and ventilated animals, in the body coil of a 1.5-Tesla whole-body (Siemens, Munich Germany) Vision prototype. Baseline anatomic images were obtained by a turboFLASH technique to identify coordinates for apical four-chamber, two-chamber, and short-axis views. For function studies, 24 sequential image frames were collected over 12 heartbeats during breath-hold using shared-center turboFLASH in each of the three standard views. After detection of the optimal inversion time (TI; typically 200 to 300 ms), a series of 32 diastolic images were acquired in the double-oblique four-chamber view during breath-hold, while injecting 0.05 mmol/kg gadodiamide (T1-reducing contrast agent). The series of images was viewed as a movie, to locate the zone with impaired contrast arrival. The short axis at the center of that zone (target zone) was prescribed graphically. All measurements were performed by two independent investigators blinded to treatment. Custom-designed software was used to define myocardial borders and measure wall thickness. End-systolic and end-diastolic left ventricular volumes were computed from biplane measurement (apical four-chamber and two-chamber views) as previously validated, and used to calculate left ventricular ejection fraction. Target wall motion (radial shortening) and target wall thickening were expressed as percentage of the radial length or wall thickness at the end of diastole. Both parameters were also measured at the septum, yielding normal target wall motion and target wall thickening. The area of delayed contrast arrival was defined as myocardium demonstrating distinctly slowed time ($\geq 1$ cardiac cycle) to half-maximal signal intensity, using a two-dimensional map of contrast intensity versus time.

MRI: left ventricular function Infarct size visualized as myocardium without MRI contrast uptake was measured to avoid confounding of regional function and perfusion measurements. Infarct size was similar among the five groups at either baseline (3 weeks) or final study (ANOVA, p=0.594 and p0.303, respectively). Infarct size, 3.0%±4.9% left ventricular area (mean±SD), was within the range reported for this model.

Left ventricular ejection fraction (EF) at baseline was similar for all treatment groups (ANOVA, p=0.120). Using each animal as its own control, EF improved significantly in controls (p=0.018), in the FGF 2 μg/kg IV (p=0.046), the FGF 6 μg/kg IV (p=0.001), and the FGF 6 μg/kg IC groups (p=0.001). The improvement in EF after treatment was significantly higher in the FGF 6 μg/kg IC (p<0.01) group compared with controls. The improvement in indexed target wall motion (target wall motion/normal wall motion) was significant only in the FGF 6 μg/kg IV (p=0.019) and the FGF 6 μg/kg IC groups (p=0.004), whereas indexed target wall thickening improved in the FGF 6 pug/kg IC group (ANOVA, p=0.007 compared with improved target wall thickening in controls, p=0.001).

MRI: perfusion. At baseline, no differences in areas of delayed arrival (ANOVA, p=0.140) or collateral extent (p=0.103) were found between the groups. The size of the zone of delayed arrival decreased in the FGF 6 μg/kg IC (p<0.001), which was significantly different from the change in controls (ANOVA, p<0.001).

Toxicologic assessment of FGF-2 administration. Before treatment and at necropsy, blood samples for hematology, coagulation, and serum chemistry were obtained from at least three fasted animals per group. Hematology parameters included hemoglobin, mean corpuscular hemoglobin concentration, hematocrit, erythrocyte count, total leukocyte count, differential, platelet count, mean corpuscular hemoglobin, and mean corpuscular volume. Serum chemistry included aspartate aminotransferase, alanine aminotransferase, gamma glutyltransferase, alkaline phosphatase, lactate dehydrogenase, total bilirubin, total cholesterol, triglycerides, blood urea nitrogen, creatinine, creatine phosphokinase, albumin, globulin, total protein, electrolytes (Na, K, and Cl), calcium, phosphorus, and glucose.

In addition, for four randomly selected animals in each treatment (not vehicle) group, tissue samples were taken from major organs and processed for histology. Histopathological findings were graded on a scale of 1 to 4 (minimal<mild<moderate<marked), by a veterinary pathologist blinded to treatment.

There were no macroscopic or microscopic lesions related to intravenous or intracoronary administration of FGF-2. Furthermore, no changes in hematological or biochemical parameters were observed in any of the treatment groups.

In this study, in which the efficacy of intravenous and intracoronary delivery of 2 or 6 μg/kg FGF-2 was compared, blood supply to the myocardium, as assessed by the colored microsphere method, was improved by the high-dose (6 μg/kg) intracoronary FGF-2. Although this effect was only significant at stress, the same trend was seen for regional blood flow at rest. Both intravenous FGF-2 doses as well as the 2-μg/kg dose were ineffective. This change in regional blood flow was confirmed by perfusion and collateral-sensitive MRI, and had functional significance because it was accompanied by an increase in EF and improvement in target wall motion and target wall thickening in the high-dose intracoronary group. The effect on EF was added to the natural tendency to grow collaterals and improve perfusion and function of ischemic myocardium.

The current study presents evidence that a single intracoronary injection of 120 to 150 μg FGF-2 improves regional blood flow as well as regional and global cardiac function. The ineffectiveness of intravenous FGF-2 might result from less favorable pharmacokinetics. Several studies have reported a 3- to 10-fold lower recovery of radiolabeled FGF-2 from the myocardium after intravenous administration than after intracoronary injection, which in turn has a lower recovery and shorter redistributiontimes than intrapericardially delivered FGF-2. FGF-2 might be retained in the myocardium by a high-capacity, low-affinity sink provided by heparin sulfates in the matrix and on the surface of endothelial cells, which are upregulated by ischemia. In addition, expression of FGF-R1 receptors, which are the primary transducers of FGF-2 signaling, is also upregulated by ischemia.

In this animal study, in accordance with the phase I clinical trial, intravenous FGF-2 and 2 μg/kg intracoronary FGF-2 had no major hemodynamic, hematologic, or biochemical side effects.

Clinical implications If a single intracoronary infusion of FGF-2 proves to be effective in patients with chronically ischemic myocardium, this strategy will greatly increase the number of patients that might benefit from adjunctive growth factor therapy, especially in view of the minimal side effects. Each patient undergoing percutaneous revascularization is a candidate for angiogenic therapy because most interventions are local and aimed at the most severe stenoses in epicardial arteries. The additional benefit of myocardial salvage during reperfusion injury by FGF-2 further emphasizes the potential value of this adjunct pharmacotherapy.

It is concluded that a single 6-μg/kg intracoronary FGF-2 delivery results in significant improvement in collateralization and regional and global function of chronically ischemic myocardium. A single intravenous infusion of FGF-2 is ineffective in the doses tested. A phase II clinical trial of patients with coronary artery disease designed to evaluate this intracoronary therapeutic strategy is currently underway.

Example 5

Local Perivascular Delivery of FGF-2

In this trial, patients with a viable and ischemic myocardial area that could not be revascularized were randomized to receive heparin-alginate pellets containing 10 or 100 μg of bFGF or placebo that were placed on the epicardial surface during CABG.

Patient Selection. The study population consisted of patients undergoing CABG at Beth Israel Deaconess Medical Center and Albert Einstein College of Medicine in Boston, Mass. The inclusion criteria included an area of myocardium supplied by a major coronary artery with advanced disease not amenable to bypass grafting or percutaneous intervention, inducible ischemia, and the ability to understand and sign the informed consent and to comply with planned follow-up. Patients with the following criteria were excluded from consideration for the study: absence of inducible ischemia or myocardial viability of the target area, hypertrophic or restrictive cardiomyopathy, left ventricular ejection fraction<20%, significant valvular heart disease, renal dysfunction (serum creatinine>2.5 mg/dL), history of malignancy within the previous 5 years, or unexplained hematological or chemical abnormalities before CABG.

The design and performance of the study were approved by the Food and Drug Administration under an investigator-sponsored investigational new drug (BB-IND 5725). The study was approved by the Committee for Clinical Investigation at both institutions. The first patient was enrolled in September 1996 and the last patient in May 1998.

Patient Population and Enrollment Procedure. Seventy-eight patients scheduled for CABG were screened for enrollment into the study on the basis of an angiogram that showed a major epicardial coronary artery (posterior descending artery, significant diagonal, obtuse marginal, or ramus intermedius branch, or significant posterolateral branch) that was considered by an interventional cardiologist and a cardiothoracic surgeon not involved in the study unlikely to be graftable on the basis of its angiographic appearance (diffusely diseased or heavily calcified). Patients were approached for enrollment in the study, and screening tests were performed to ensure that all eligibility criteria were met, including demonstrable ischemia in the target myocardial area.

Forty-six patients who met all eligibility criteria and agreed to participate in the study underwent CABG, during which a noninvestigator cardiac surgeon determined whether the target area was indeed ungraftable. Bypass surgery of the target vessel was performed in 22 cases, and those patients were excluded from additional study. The remaining 24 patients (19 patients at Beth Israel Deaconess Medical Center and 5 at Montefiore Medical Center, Bronx, N.Y.) who had a coronary artery that could not receive a graft at the time of surgery were randomized to receive 10 heparin-alginate pellets containing placebo or 1 of 2 doses of bFGF (10 or 100 μg). There was no significant difference between the study groups in any of the clinical parameters, including the extent of coronary disease or presence of any risk factor, except that patients in both 10- and 100-μg bFGF treatment groups were somewhat older than controls, and there were more women in the 10-μg bFGF group. The baseline resting ejection fraction was 50.3±13.8%, and 5 of the 24 patients had an ejection fraction<30%.

Preparation of bFGF-Containing Heparin-Alginate Pellets. Calcium alginate pellets provide a stable platform for bFGF because of enhanced retention of activity and storage time and thus were used as devices for controlled bFGF release in vivo. Heparin-sepharose beads (Pharmacia LKB) were sterilized under ultraviolet light for 30 minutes and then mixed with filter-sterilized sodium alginate. The mixed slurry was dropped through a needle into a beaker containing a hardened solution of $CaCl_2$ (1.5% wt/vol). Beads formed instantaneously. Uniformly cross-linked capsule envelopes were obtained by incubating the capsules in the $CaCl_2$ solution for 5 minutes under gentle mixing and then for 10 minutes without mixing. The beads were washed with sterile water and stored in 0.9% NaCl-1 mmol/L $CaCl_2$ at 4° C. bFGF loading was performed by incubating 10 capsules in 0.9% NaCl-1 mmol/L $CaCl_2$-0.05% gelatin with 12.5μ (for 10-μg dose) or 125μ (for 100-μg dose) of bFGF (GMP grade human recombinant bFGF provided by Scios, Inc) for 16 hours under gentle agitation at 4° C. Previous studies have shown that under these conditions, 80% of bFGF in solution is absorbed into heparin-alginate pellets. The end product was sterilized under ultraviolet light for 30 minutes. With each preparation, several beads were cultured to ensure sterility. Blank or bFGF-loaded pellets were identical in appearance, which ensured that the surgeons and investigators were blinded with regard to which pellet was being used.

bFGF Heparin-Alginate Delivery After completion of coronary bypasses to all areas of the heart that could be revascularized and failure to-graft the target vessel (which on occasions involved probing of the target vessel), multiple linear incisions were made in the epicardial fat surrounding the target vessel. Heparin-alginate pellets (containing bFGF or placebo) were inserted into the epicardial fat overlying the artery and secured in place by a 6.0 prolene suture to close the subepicardial incision. A total of 10 pellets were used in each patient (2 to 3 pellets were placed in each incision). The left internal mammary artery (LIMA) was placed on the left anterior descending artery (LAD), and proximal vein-to-aorta anastomoses were constructed. Ventilation was reestablished, and cardiopulmonary bypass was terminated. Routine closure was then performed.

Short-Term Results. The extent of CABG surgery was the same in all treatment groups; there were no significant differences with regard to the number of grafts, duration of surgery (average 3.0±0.9 hours), or cross-clamp time (average 56±13 minutes). The target vessel was the right coronary artery (RCA) in 15 patients, left circumflex artery in 7, and diagonal branch of the LAD in 2.

One patient in the control group died 24 hours after surgery secondary to an autopsy-documented occlusion of one of the saphenous vein grafts, with a large myocardial infarction in that territory. A second death occurred in a patient in the 100-µg bFGF group who could not be weaned off cardiopulmonary bypass (preoperative ejection fraction of 20%); an autopsy revealed patent grafts with extensive myocardial scarring and a thin rim of epicardial viable myocardium. Two other patients (both in the control group) required intra-aortic balloon pump support after surgery (in 1 patient, the intra-aortic balloon pump was inserted before surgery). Two patients (1 in the control group and 1 in the 10-µg bFGF group) had a Q-wave myocardial infarction in the target myocardial distribution, and 1 patient in the 10-µg bFGF group had a Q-wave myocardial infarction in a nontarget myocardial distribution.

Placement of bFGF-containing heparin-alginate microspheres had no significant short-term effects on blood pressure or heart rate; the mean arterial pressure was 84.8±10.6 mm Hg before bypass, 89±12 mm Hg on day 1, 93±7 mm Hg on day 3, and 83.4±11.1 mm Hg on day 5 and was not different among the treatment groups. Pharmacokinetic evaluation did not reveal any significant increase in serum bFGF levels above baseline in any of the groups (average bFGF levels in 15 patients: 17.4±3.3, 15.90±1.4, 15.9±1.8, and 16±1.8 µg/mL at baseline and postoperative days 1, 3, and 5, respectively), and there were no significant differences in bFGF levels between the different treatment groups. The average postoperative hospital stay was 5.30±1.3 days (range 4 to 8 days). There were no acute effects on serum chemistries, hematologic and coagulation profiles, liver function tests, or urinalysis. Two patients developed superficial wound infections along the chest incision that necessitated surgical debridement, and another patient with diabetes mellitus had delayed healing of the saphenous vein graft harvest site. Microbiological evaluation of the beads showed no aerobic or anaerobic growth in samples from 28 of the 46 preparations.

In-Hospital Follow-Up. The postoperative course was evaluated, including hemodynamic parameters, duration of ventilatory support, postoperative ECGs, postoperative cardiac isoenzymes, duration of hospitalization, and any evidence of infection. Serum bFGF levels were measured (ELISA, R&D Systems) before implantation and on the first, third, and fifth postoperative days. Complete blood count, coagulation parameters, serum chemistries, and urinalysis were performed before treatment and at days 3 and 5 after treatment. In the first 10 patients, stress nuclear perfusion imaging and MRI (at the Beth Israel Deaconess Medical Center) were performed before CABG; however, owing to the confounding effect of CABG (realized after an interim analysis of the first 10 patients by the Data Safety and Monitoring Committee), the remaining patients underwent stress nuclear perfusion scans (rest-thallium/dipyridamole sestamibi) and MRI after CABG (before discharge). The surgeon, other investigators, and patients were blinded to treatment assignment.

Long-Term Follow-Up. All patients were contacted by the investigators at 6 weeks; 2, 3, 4, and 6 months; 1 year; and then yearly thereafter to assess clinical events (death, myocardial infarction, recurrent angina, or any repeat revascularization). Complete blood count, coagulation parameters, serum chemistries, urinalysis, and serum bFGF level measurements were repeated at 3 months. Patients underwent stress nuclear scans at 3 months (dual-isotope studies with rest thallium and stress [pharmacological stress with dipyridamole sestamibi]). In addition, patients at the Beth Israel Deaconess Medical Center underwent repeat MRI 3 months after CABG. Clinical follow-up of ≧6 months was available for-all patients, with a mean follow-up of 16.0±6.8 months.

Clinical Follow-Up. Clinical follow-up was available in the 22 surviving patients (7 from the placebo group, 8 from the 10 µg-bFGF group, and 7 from the 100 µg-bFGF group) and averaged 16.0±6.8 months. At last follow-up, all patients were angina-free except for 3 patients in the placebo group (Canadian Cardiovascular Society [CCS] class II in 1 and class III in 2 patients) and 1 patient in the 10-µg bFGF group (CCS class II). Two of the 3 placebo patients with angina underwent successful percutaneous revascularization (1 involved the target vessel and the second involved a vein graft stenosis). After hospital discharge, none of the patients died or sustained a myocardial infarction. There were no delayed wound infections, no clinical evidence of pericarditis, and no other adverse events. Laboratory evaluation at 90 days (available in 21 patients) did not show any adverse effect on complete blood count, coagulation parameters, serum chemistries, or urinalysis.

Imaging Studies. Rest thallium/dipyridamole sestamibi studies were performed according to the ADAC protocol. We compared baseline and 90-day nuclear scans using the size of the stress perfusion defect, as determined by pixel analysis. MRI was performed in the body coil of a 1.5-T whole-body Siemens Vision system. Baseline anatomic images were obtained by a turboFLASH (turbo Fast Low-Angle SHot) technique to identify coordinates for apical 4-chamber, 2-chamber, and short-axis views. Functional imaging was performed during breathhold by use of shared-center turboFLASH in each of the 3 mutually perpendicular standard views, producing 24 sequential image frames each, collected over 12 heartbeats to measure regional wall motion. MR perfusion imaging was performed as follows: a series of 4 inversion recovery images (1 every second heartbeat) was obtained as inversion time (TI) and adjusted to minimize the signal intensity from myocardium in the fourth frame. With the best TI determined by these scout images, a series of concurrent parallel images were acquired in diastole during breathhold, 1 every other heartbeat, at baseline and again with contrast injection (0.05 mmol/kg gadodiamide). In addition, complete blood count, coagulation parameters, serum chemistries, urinalysis, and serum bFGF level measurements were repeated at 3 months.

Nuclear Perfusion Imaging. Twenty of the surviving 22 patients underwent stress nuclear perfusion imaging 90 days after CABG. In the first 10 patients, baseline studies were performed before CABG. It became clear as the study progressed, however, that this was not a true baseline because of the confounding effect of CABG. Therefore, in the remaining 12 patients, rest-thallium/dipyridamole sestamibi nuclear testing was performed after CABG and before hospital discharge. The baseline stress target area defect size was 20.6±5.2% of the left ventricle and was similar in all 3 treatment groups (22.3±5.4% in controls, 19.2±5.0% for the 10-µg bFGF group, and 20.4±5.7% for the 100-µg bFGF group, ANOVAP=0.56). At the time of follow-up nuclear scans, when paired t tests were used, there was a trend toward worsening (increase in the defect size) in the placebo group (20.7±3.7% at baseline to 23.8±5.7% at follow-up, P=0.06). Studies in the 10-µg bFGF group showed no change in defect size(19.2±5.0% to 16.9±8.1%, P=0.39), whereas defect size in the 100-µg bFGF group was significantly improved compared with baseline (19.2±5.0% to 9.1±5.9%, P=0.01). The change in defect size was significantly different among the 3 groups (ANOVA P=0.005). Semiquantitative analysis of stress images demonstrated worsening of the defect in 3 of 6 patients and no change in 3 of 6 patients in the control group. Of 8 patients in the 10-µg bFGF group, the target nuclear defect size worsened in 2 patients, remained unchanged in 2, and improved in 4. Finally, of the 6 patients in the 100-µg bFGF group who underwent follow-up nuclear testing, there was improvement in 5 patients and no change in 1 patient.

Magnetic Resonance Imaging. Functional and perfusion MRI were performed in 8 patients at the Beth Israel Deaconess Medical Center at baseline and at 90-day follow-up (4 controls and 4 bFGF-treated patients [1 patient in the 10-µg bFGF group and 3 in the 100-µg bFGF group]). Baseline resting target wall motion (radial wall motion) was 21.7±6.7% in the placebo group and 27.3±17.0% in patients treated with 100 µg of bFGF (compared with 35.7±10.9% for normal revascularized wall). No changes in resting target wall motion were seen at follow-up (23.7±9.3% in placebo and 32.3±12.4% in 100-µg bFGF-treated subjects). The extent of the resting delayed contrast arrival zone, which reflects underperfused myocardium, for placebo and bFGF-treated patients was 10.7±3.9% and 15.7±2.3% at baseline and decreased to 7.8±6.9% (P=0.37) and 3.7±6.3% (P=0.06) at follow-up, respectively, with a trend toward improvement in the 100-µg bFGF group.

Because of the protracted course of new collateral development, the potential for hemodynamic disturbances associated with bolus intravascular delivery, and the possibility for toxicity from elevated circulating levels of angiogenic growth factors, a local sustained bFGF delivery strategy using heparin-alginate microcapsules was used. This delivery system allows prolonged (4 to 6 weeks) sustained release (first-order kinetics). In animal studies, there was a dose-dependent effect of bFGF that was not associated with detectable serum levels, hemodynamic effects, or local or systemic toxicity.

Of the 46 patients judged to have a major coronary artery that could not be grafted on the basis of angiographic appearance, 22 patients were actually successfully grafted at the time of CABG. Thus, preoperative assessment of arterial suitability for bypass proved to be inaccurate in almost 50% of cases. In accordance with prior observations, the major epicardial artery most likely to be unsuitable for grafting was the RCA. In no case was the LAD considered ungraftable. This paucity of LAD cases is probably a reflection of the reluctance to refer those patients in whom the LAD may not be bypassed for surgical intervention.

The combination CABG/bFGF therapy was not associated with an excess rate of complications. Two operative deaths in this study most likely reflect the higher operative risk in patients with advanced coronary disease and left ventricular dysfunction who have incomplete revascularization. The absence of hemodynamic abnormalities associated with heparin-alginate bFGF delivery is consistent with the undetectable serum levels of bFGF at any time after growth factor administration. In addition, the lack of short- or intermediate-term adverse effects on serum chemistries, hematologic profile, liver function tests, or urinalysis also suggests that this mode of delivery is not associated with systemic toxicity. These observations therefore emphasize the safety of heparin-alginate bFGF delivery at the time of CABG.

this randomized, double-blind, placebo-controlled study of bFGF in patients undergoing CABG demonstrates the safety and feasibility of this mode of therapy in patients with viable and ischemic but unrevascularizable myocardium. These results warrant a larger multicenter trial to assess the clinical benefit of this combination approach to myocardial revascularization, which is currently under way.

Example 6

Reduction in Myocardial Infarct Size Following Intracoronary Administration of FGF-2

The extent of myocardial injury and necrosis resulting from an ischemic insult is determined by the duration of interruption to antegrade flow, the size of the compromised territory, and the extent of collateral circulation to the region. In view of the beneficial effects on myocardial viability and contractile function demonstrated in collateralized patients with occlusive coronary artery disease, these findings provide a rationale for investigation of new strategies that use growth factors such as bFGF to pharmacologically enhance collateral growth and to blunt the effects of impaired antegrade myocardial perfusion.

Coronary Occlusion and Reperfusion. Twenty-two mongrel dogs of either sex (weight, 17 to 23 kg) were randomly assigned to treatment with bFGF or vehicle. After the animals received anesthesia with sodium pentobarbital (25 mg/kg IV), intubation, and ventilation with room air, the right carotid artery was exposed, ligated distally, and cannulated. Aortic blood pressure, heart rate, and ECG were monitored continuously throughout the procedure. After baseline left ventriculography was accomplished via a 6F pigtail catheter, selective left coronary angiography was performed via an 8F angioplasty guiding catheter. Because of the potential interaction between heparin and bFGF, intraprocedural anticoagulation was achieved with the use of Hirulog, a synthetic direct thrombin inhibitor; after an intravenous loading dose of 2.5 mg/kg, intravenous infusion was commenced at 5 $mg \cdot kg^{-1} \cdot h^{-1}$ and the rate adjusted to maintain the activated clotting time at >300 seconds.

An angioplasty balloon catheter (balloon:artery ratio 1.0) was then inflated at 2 atm in the middle part of the LAD distal to the first diagonal branch, and occlusion was confirmed angiographically. After 4 hours' occlusion, the balloon catheter was deflated and removed, and LAD patency was confirmed angiographically. Ten micrograms of human recombinant bFGF (in 20 mmol/L sodium citrate, 1 mmol/L EDTA, and 9% sucrose, pH 5; Scios Nova Inc) in 10 mL normal saline or vehicle (10 mL normal saline) was administered directly into the left main coronary artery via the guiding catheter 10 minutes after occlusion and again just before reperfusion. After reperfusion, left ventriculography was repeated. All surgical procedures were performed with the use of a sterile technique. Seven days after the first procedure, dogs were anesthetized, intubated, and ventilated in the same manner as before. Patency was confirmed angiographically, left ventriculography was repeated, and euthanasia was performed with a lethal dose of pentobarbital.

Figure 4:
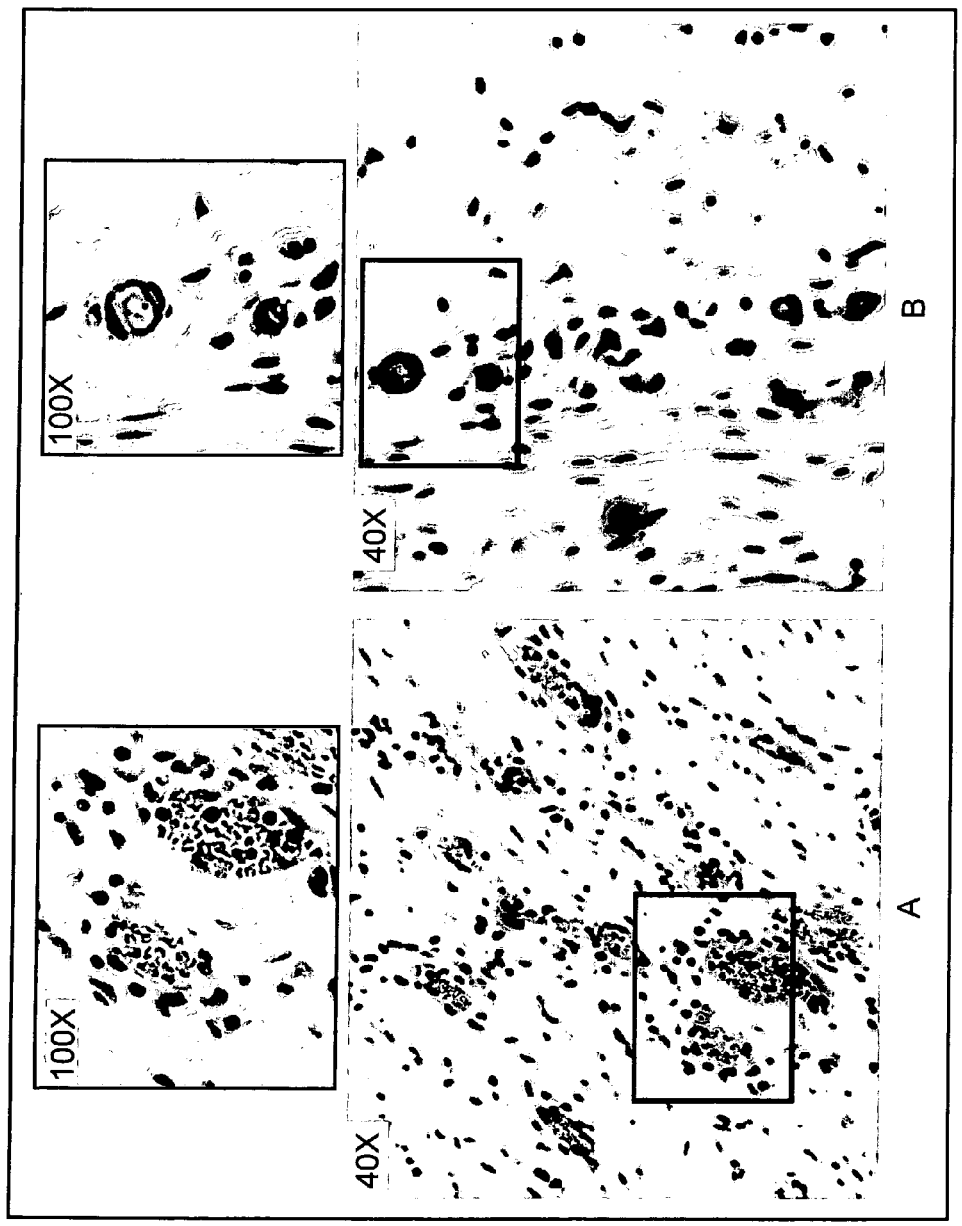

Occlusion-Reperfusion Study. Blood pressure and heart rate were similar in both groups throughout the experiment. Heart rate was increased during reperfusion in vehicle- and in bFGF-treated dogs (both P=0.043 versus baseline) because of nonsustained ventricular tachycardia and frequent ventricular ectopic activity. No systemic hemodynamic changes were noted after bFGF was administered. The areas at risk were similar in both groups (41±8 $cm^2$ versus 40±6 $cm^2$, vehicle versus bFGF). In the bFGF-treated group, infarct size expressed as a percentage of the area at risk was 13.7±2.1%, which was significantly less than in dogs receiving vehicle(28.4±3.4%; P=0.002; FIG. 3▫). At baseline, left ventricular ejection fractions were similar in both groups (bFGF versus vehicle, 42.6±1.9% versus 44.8±3.5%). After reperfusion (bFGF versus vehicle, 33.1±5.4% versus 40.3±3.2%) and again at 1 week after infarction (bFGF versus vehicle, 33.6±3.6% versus 38.8±3.5%), ejection fractions showed no significant difference between groups (FIG. 4▫).

Microscopic examination of sections demonstrated concordance between triphenyltetrazolium chloride infarct delineation and histological features of myocardial necrosis. Although bFGF treatment was associated with significant myocardial salvage, there was no difference in the number of endothelial cells per high-power field within the infarcted region (bFGF versus vehicle, 241±16 versus 221±18 cells/hpf; P=0.8) or in the number of endothelial cells in the border zones (bFGF versus vehicle, 247±18 versus 245±15 cells/hpf; P=0.63). Because of the potential for spurious PCNA counts in areas of leukocyte infiltration, PCNA counts were obtained from border zones only; these counts were similar in both groups (bFGF versus vehicle, 10.1±2.3 versus 7.3±2.3 cells/hpf; P=0.4).

Measurement of Activated Clotting Time. Activated clotting time was measured with the use of the Hemochron 801 timer (International Technidyne Corp). After 2 mL of whole blood was collected into a Hemochron tube containing 12 mg of Johns-Manville diatomaceous earth, the time taken to completecoagulation at 37° C. was measured.

Delivery and Biological Activity of bFGF. To ensure delivery of bFGF after passage through the manifold and angioplasty guiding catheter, radiolabeled bFGF was passed through new and used systems. To simulate the conditions of an in vivo experiment, 20 µg of cold bFGF was mixed with 25 µCi of radiolabeled bFGF in 20 mL of normal saline solution. A second batch of 20 µg of cold bFGF was mixed with 25 µCi of radiolabeled bFGF in 20 mL of normal saline solution containing 1 mg/mL of dog albumin (Sigma Chemical Co). The number of counts per minute from both solutions was quantified in a scintillation counter. Ten-milliliter aliquots of the radiolabeled solutions were then delivered through used and new guiding catheters and manifolds and flushed with an additional 10 mL of normal saline. The number of counts per minute in the solutions collected after passage through the catheter system was measured. The difference in counts per minute between the incoming and outgoing solution was used as an index of bFGF loss within the delivery system. Under the conditions described above, there was minimal loss of activity in the delivery system. The bFGF used in the experiments was compared in a mitogen assay with human recombinant bFGF from a commercial source (Boehringer Mannheim) that had proven activity in previous assays. The potency of both lots of bFGF was similar, as assessed by $^3$H-thymidine uptake after stimulation of cultured human fibroblasts (data not shown).

Determination of Infarct Size. After euthanasia and rapid excision of the heart, the LAD and circumflex arteries were cannulated individually. Simultaneously, at a pressure of 100 mm Hg, the circumflex vessel was perfused with Evans blue dye and the LAD with triphenyltetrazolium chloride for 10 minutes. Hearts were then fixed by perfusion with Histo-Choice (Ameresco) for 4 hours, after which the left ventricle was cut into 1-cm-thick slices perpendicular to its long axis, and the slices were weighed. With this technique, areas of viable tissue in the LAD distribution are stained red, necrotic areas remain white, and the circumflex territory is stained blue. For each slice, the area at risk, the area of infarction, and the circumflex territory were determined by computer-assisted planimetry, as previously described.

Histology and Immunohistochemistry. Multiple tissue samples were taken from areas of infarction and areas at risk of infarction for histological examination to seek evidence of neovascularization. Given the assumptions that (1) neovascularization of ischemic regions would proceed from the circumflex and nonoccluded LAD distributions and (2) the tissue stimulus for neovascularization would be intense in tissue adjacent to the infarct zone, "border-zone" samples were taken from the area at risk midway between the edges of the macroscopically infarcted myocardium and the junction of the LAD and circumflex territories. Staining with hematoxylin and eosin was used to confirm the presence of tissue necrosis in the infarct zones. Immunohistochemical staining of tissue samples was performed with factor VIII-related antigen to detect endothelial cells and PCNA to detect proliferating cells.

After being embedded in paraffin, 5-µm sections were cut and collected onto glass slides coated with 1% polychloroprene in xylene. After being dried for 60 minutes at 60° C., paraffin was removed in three changes of xylene. The tissue was then rehydrated through graded alcohols before being rinsed in PBS. Immunohistochemical staining was performed in a Jung Histostainer (Leica). A 0.6% hydrogen peroxide solution in PBS was then applied for 5 minutes to remove any endogenous peroxidase. For the PCNA sections, a blocking solution of 1:10 (vol/vol) normal rabbitserum (Dako Corp) was added for 10 minutes before application of a 1-in-50 dilution of murine monoclonal antibodies directed against PCNA (PC10 Clone, Dako Corp). For the factor VIII-related antigen stain, a blocking solution of 1:10 (vol/vol) normal swine serum (Dako Corp) was added for 10 minutes before application of a 1:300 dilution of rabbit polyclonal antibodies directed against factor VIII-related antigen (Dako Corp). The dilutions of the primary antibodies were prepared with the use of 1% BSA in PBS and were incubated with the tissue sample at 30° C. for 60 minutes. A 1:200 dilution of biotinylated rabbit anti-mouse polyclonal antibody (Dako Corp) was then added for 30 minutes to the PCNA sections, and 1:200 biotinylated swine anti-rabbit polyclonal antibody (Dako Corp) was added to the factor VIII-stained sections for 30 minutes. These antibodies were labeled with an Elite streptavidin-biotin-peroxidase complex (Vector Laboratories) applied for 30 minutes. The final stage involved the addition of 3,3'-diaminobenzidine (Vector Laboratories) as a chromogen. Between steps, the sections were rinsed for 2 minutes in PBS. Slides were then rinsed in distilled water, dehydrated, cleared in xylene, and mounted in Permount (Fisher Scientific). In each staining preparation, sections treated with 1% BSA in PBS instead of with the primary antibody were included as negative controls, and sections of human tonsil were used as positive controls.

Cell Counts. Photographs of immunohistochemically stained tissue sections were taken without knowledge of treatment assignment. After low-power examination, five to seven representative fields (0.5×0.34 mm) were photographed from each section at a magnification of 200×. Whenever possible, consecutive adjacent fields were photographed. In sections from the infarct zone, fields with relative preservation of tissue architecture were selected, obviating spurious increases in vessel density due to preservation of vascular structures in areas of parenchymal loss and stromal collapse. Cells that stained positive for PCNA and factor VIII (regardless of the presence of a vascular lumen) were counted by two independent observers blinded to treatment assignment (interobserver correlation coefficient, r=0.69; P<0.0001). Immunostaining for factor VIII and PCNA represented the techniques currently used as diagnostic tools for measurement of tumor angiogenesis.

Left Ventricular Ejection Fraction. Left ventricular ejection fractions were determined from single-plane left ventriculograms measured by a trained technician who was blinded to treatment assignment. Ejection fractions were calculated by use of the length-area method with a computer analysis package (Angiographic Ventricular Dynamics 5.1, Siemens).

Acute Hemodynamic Studies In five additional dogs of either sex (weight, 19 to 22 kg), we compared the effects of intracoronary bFGF on coronary hemodynamic parameters with those of temporary coronary occlusion and intracoronary NTG. The studies were performed with the use of a standard open-chest model in which the LAD was isolated and instrumented with a Doppler flow probe to measure blood flow (Crystal Biotech). A 2F catheter was advanced retrogradely via a small proximal branch of the LAD into the left main vessel for administration of drugs. Blood flow responses after 10- and 20-second periods of LAD occlusion and after incremental doses of intracoronary NTG (1, 10, and 100 µg) were recorded to confirm the presence of coronary vascular reactivity. Incremental doses of intracoronary bFGF (1, 10, and 100 µg) were then given, and coronary flow responses were measured. bFGF (buffered as described above) and NTG solutions were prepared in 1 mL of normal saline just before administration and were given as boluses over 20 seconds. Blood pressure, heart rate, and ECG were monitored continuously throughout the procedure. Coronary vascular resistance (CVR) was calculated according to the formula $$CVR(mmHg \cdot mL^{-1}) = \text{mean aortic pressure (mm Hg)} \times 1/\text{coronary flow (mL/min)}$$

The results of the occlusion-reperfusion study demonstrated a reduction in infarct size without histochemical evidence of myocardial neovascularization. The acute hemodynamic study was performed to assess the presence of a vasodilator action of bFGF as described in dogs and other species whereby flow to the infarct zone could possibly be augmented by an increase in the conductance of preexisting collateral channels, independently of neovascularization. In the five dogs studied, coronary blood flow and coronary vascular resistance were unchanged after incremental pharmacological doses of intracoronary bFGF despite pronounced vasodilator responses to 10- and 20-second coronary occlusion and intracoronary NTG. In addition, three of the dogs were monitored for 30 minutes after the final dose of bFGF (100µg) to detect the presence of a delayed vasodilator response as reported previously. No significant hemodynamic changes were observed in response to bFGF during the experiment.

Institutional Approval and Sample Size. The protocol was approved by the Cleveland Clinic Foundation Institutional Review Board and Animal Research Committee. Animals were handled in accordance with the National Institutes of Health guidelines for the use of experimental animals. In the occlusion-reperfusion study, 22 dogs were randomized to receive bFGF or vehicle. Five dogs (2 treated with bFGF, 3 with vehicle) died of arrhythmias before completion of the protocol. Three dogs (1 treated with bFGF, 2 with vehicle) were excluded because of persistent occlusion at the site of balloon occlusion. No dogs were excluded from the acute hemodynamic study.

Data Analysis. All data are expressed as mean±SEM. Differences between groups were evaluated by use of two-tailed, unpaired t tests. The Pearson correlation coefficient was used to assess inter-observer variability for cell counts. Repeated measurements of left ventricular ejection fraction were compared by use of two-way ANOVA. Differences were considered significant at a value of P<0.05.

This study has demonstrated that bFGF reduces the extent of infarction in the canine occlusion-reperfusion setting. Although there is little doubt that the beneficial effects of bFGF on coronary perfusion in chronic ischemia are mediated principally by its angiogenic actions, we have demonstrated that myocardial salvage occurs independently of neovascularization after administration of bFGF in the setting of acute myocardial infarction. Further evaluation of coronary vasomotor responses to bFGF in ischemic and nonischemic settings and investigation of the potential cytoprotective properties of bFGF in acute ischemia promise to provide fertile and clinically relevant areas for future investigation.

Example 7

Intracoronary and Intravenous Administration of FGF-2

This study was designed to investigate the myocardial and tissue deposition and retention of bFGF after IC and i.v. administration in normal and chronically ischemic animals.

Tissue distribution studies were carried out in 24 Yorkshire pigs (12 normal animals and 12 chronically ischemic animals). Yorkshire pigs of either sex weighing 15 to 18 kg were anesthetized with i.m. ketamine (10 mg/kg) and halothane inhalation anesthesia. By sterile technique, a right popliteal cut down was performed and a 4 French arterial catheter was inserted for blood sampling and pressure monitoring. Left thoracotomy was performed through the 4th intercostal space during mechanical ventilation. The pericardium was opened and an ameroid constrictor of 2.5 mm internal diameter (matched to the diameter of the artery) was placed around the proximal left circumflex coronary artery. The pericardium was closed using 6/0 Prolene and the chest was closed. A single dose of i.v. cefazolin (70 mg/kg) was given and i.m. narcotic analgesics were administered as needed. Animals were then allowed to recover for 3 weeks (time sufficient for ameroid closure) before radiolabeled growth factor delivery. The treatment of animals was done according to National Institutes of Health guidelines and the protocol was approved by the Institutional Animal Care and Utilization Committee of the Beth Israel Deaconess Medical Center.

A total of 24 animals was used for the study. Twelve animals underwent ameroid placement on the LCX, and 3 weeks later, after confirming LCX occlusion angiographically, received $^{125}$I-bFGF. IC $^{125}$I-bFGF was administered to six normal and six ischemic animals, whereas i.v. $^{125}$I-bFGF was given to six normal and six ischemic animals. Tissue deposition was measured at 1 and 24 h in three animals of each group. The use of these two time points was determined by the need to study more sustained myocardial deposition and retention of $^{125}$I-bFGF.

Ischemic animals (three weeks after ameroid placement) and normal noninstrumented animals were anesthetized with i.m. ketamine (10 mg/kg) and halothane inhalation anesthesia. By sterile technique, an i.v. line was inserted into the ear vein and a right femoral cut down was performed to introduce an 8Fr arterial sheath. Coronary angiography was then performed in multiple views using a 7 French JR4 diagnostic catheter (Cordis Laboratories, Inc., Miami, Fla.) to confirm LCX occlusion in ischemic animals and to assess the coronary anatomy. $^{125}$I-Bolton Hunter-labeled bFGF ($^{125}$I-bFGF; 25 µCi; New England Nuclear) with a specific activity of 110 µCi/µg (4050 kBq/µg) was combined with 30 µg of cold bFGF and 3 mg of heparin (similar to the dose used in animal studies and in the recent phase I IC and i.v. human study) and was used for IC (six normal and six ischemic animals) and i.v. (six normal and six ischemic animals) delivery. For IC delivery, $^{125}$I-bFGF was infused in the left main coronary artery over 10 min. For i.v. delivery, $^{125}$I-bFGF was infused through the ear vein i.v. line over 10 min. Animals were then sacrificed 1 (n=12) and 24 h (n=12) after $^{125}$I-bFGF administration.

Extracardiac Deposition. Biodistribution of the i.v. and IC radiolabeled bFGF was determined at 1 and 24 h after administration and was pooled for ischemic and nonischemic animals. There were no significant differences between ischemic and nonischemic animals at each time point and the data was therefore pooled. At 1 h, the liver accounted for 37.6±17.1% of the total administered activity for IC and 42.1±17.7% for i.v. delivery (p=0.6), with a reduction to 2.8±1.5% for IC and 1.5±0.9% for i.v. delivery by 24 h (p=0.09). Total specific activity (1 h) in the kidneys was 2.3±1.3% for IC and 2.5±1.0% for i.v. delivery (p=0.8). By 24 h, total kidney specific activity decreased to 0.1±0.05% for IC and 0.2±0.09 for i.v. delivery (p=0.1). Finally, for IC and i.v. delivery, total lung specific activity was 2.7±4.1 and 3.8±2.6% at 1 h (p =0.6) and 0.2±0.2 and 0.4±0.08% at 24 h (p=0.05), respectively. Specific activity for urine was 0.01±0.01% for IC and 0.005±0.01% for i.v. administration at 1 h and increased to 0.02±0.01% for IC and 0.03±0.05% at 24 h for i.v. delivery, however, that increase was not statistically significant.

Cardiac Deposition. Total specific activity (1 h) was 0.88±0.89% for IC and 0.26±0.08% for i.v. administration (p=0.12) and decreased to 0.05±0.04% (p=0.05, compared with 1 h values) and 0.04±0.01% (p<0.001, compared with 1 h values) at 24 h, respectively. There were no differences between epicardial and endocardial deposition for both IC delivery; the results were pooled for further analysis. For IC delivery, LAD territory activity per gram of tissue (1 h) was 0.01±0.007% and 0.008±0.008% for normal and ischemic animals, and at 24 h dropped to 0.0005±0.0009% (20-fold reduction) in nonischemic animals and 0.0008±0.0005% (10-fold reduction) in ischemic animals. For i.v. delivery, 1-h LAD territory activity per gram of tissue was 0.003±0.001% (3-fold reduction, p=0.2, compared with IC) and 0.002±0.0009% (4-fold reduction, p=0.3, compared with IC) for normal and ischemic animals, and at 24 h dropped to 0.0004±0.0001% (7.5-fold reduction) in nonischemic animals and 0.0004±0.0004% (5-fold reduction) in ischemic animals, respectively. For 1-h LCX myocardial deposition, IC and i.v. deliveries resulted in a specific activity per gram of tissue of 0.008±0.004% and 0.003±0.001% (2.6-fold reduction, p=0.09) in normal animals and 0.01±0.007% and 0.003±0.001% (3.3-fold reduction, p=0.2) in ischemic animals, respectively. At 24 h, LCX deposition for IC and i.v. delivery dropped to 0.0006±0.0008% and 0.0005±0.0002% in normal animals and 0.0006±0.0006% and 0.0004±0.0004% in ischemic animals, respectively. For all groups, RCA myocardial distribution was similar to LAD and LCX distribution for i.v. administration. However, for IC delivery, RCA myocardial deposition was significantly lower than LAD or LCX myocardial deposition, because the radiolabel was infused in the left main coronary artery. Finally, for IC delivery, LCX/LAD territory activity was 79 and 154% for nonischemic and ischemic animals at 1 h and 116% and 75% for nonischemic and ischemic animals at 24 h, respectively. Intravenous administration resulted in an LCX/LAD activity of 97 and 100% for nonischemic and ischemic animals at 1 h and 123% and 98% for nonischemic and ischemic animals at 24 h, respectively.

Myocardial autoradiography confirmed myocardial deposition for both IC and i.v. delivery with three times enhanced deposition for IC delivery compared with i.v. delivery at 1 h with near equalization of tissue deposition at 24 h (measured using densitometric analysis). In addition, IC delivery resulted in increased deposition in LAD and LCX deposition compared with RCA (noninfused territory) deposition, whereas i.v. delivery resulted in a more uniform distribution in the three myocardial territories by qualitative analysis. Light level autoradiography after 72-h exposure showed LAD endothelial deposition for IC delivery after 1 h. Evaluation of other arteries for IC delivery at 24 h and for all coronary arteries at all time points failed to show $^{125}$I-bFGF deposition even after 96 h of exposure.

Duplicate plasma, urine (spot samples), and tissue samples from the liver, lung, kidney, and quadriceps muscle were obtained. Tissues were washed three times in saline to avoid contribution of radioactivity in blood. The heart, liver, lungs, and kidneys were weighed to determine total organ weight. Duplicate samples were also obtained from the right ventricle and from the proximal portion of the left anterior descending coronary arteries (LADs) and right coronary arteries (RCAs). A 1-cm mid left ventricular transverse slice was sectioned and cut into eight segments; each segment was divided into epicardial, mid-myocardial, and endocardial portions. $^{125}$I-bFGF activity was determined in a gamma counter (LKB Instruments, Inc., Gaithersburg, Md.). Background was subtracted and the amount of $^{125}$I-bFGF deposited within a specific sample was calculated as a percentage of the total activity administered. Total solid organ deposition was calculated by multiplying the specific activity per gram of tissue by the weight of the organ. Trichloroacetic acid precipitation was performed to determine specific activity, which averaged 86.3±24.4%. A 2-mm transverse left ventricular section was obtained for organ level autoradiography and exposed in a phosphoimager for 24 h. In addition, tissue samples were obtained from the LAD and the subtended myocardium, formalin-fixed, paraffin-embedded, and 10 μm sections were mounted on a slide, coated by a photographic emulsion for 72 h, developed, and examined using light level microscopy.

Data are expressed as mean±S.D. Continuous variables were compared by unpaired Student's t test, whereas categorical variables were compared by $X^2$ analysis. All reported p values were two-tailed; $p \leq 0.05$ was considered statistically significant.

Both IC and i.v. delivery strategies resulted in the majority of radiolabel being deposited in the liver. Surprisingly, liver deposition was similar for both techniques, indicating significant recirculation for IC delivery. In addition, these results confirm the previous observation that the liver is the major organ of elimination with circulating bFGF binding to -2-macroglobulin, which in turn is internalized by receptors on Kupffer. This result was duplicated for renal and lung deposition. It is important to point out that bFGF was infused in the ear vein (above the diaphragm). However, this simulates i.v. delivery in patients where the port of entry would probably be an upper extremity vein bypassing the liver first pass mechanism. Therefore, IC delivery does not result in less systemic deposition, probably due to high recirculation.

One-hour total and regional myocardial deposition was 3- to 4-fold higher for IC compared with i.v. delivery, and deposition dropped by 5- to 20-fold at 24 h. IC delivery resulted in higher deposition in ischemic myocardium, possibly related to the increased expression of fibroblast growth factor receptors associated with myocardial ischemia. This was not seen in i.v. delivery, possibly related to the initial concentrations delivered to the ischemic myocardium. Thus IC delivery, by providing higher initial concentrations in the coronary circulation, may result in higher deposition in ischemic areas. These comparisons, although consistent, did not reach statistical significance due to the small number of animals studied.

Of note, IC delivery resulted in enhanced bFGF deposition compared with i.v. delivery only in myocardial territories subtended by the infused artery. Therefore, for IC delivery to provide an advantage over i.v. delivery, infusion should be carried out in all coronary arteries and bypass grafts if present. Whether infusing a larger dose of bFGF would result in similar myocardial deposition to IC delivery (a more invasive approach) was not investigated. For IC delivery, bFGF was identified on the endothelial cells of the infused arteries, where it might exert its effect. In addition, this study raises an important question of whether more local or sustained delivery is necessary for bFGF effect, particularly with the relatively low cardiac deposition for both delivery modalities.

Example 8

Administration of FGF, VEGF and Related Growth Factor Proteins by Oral Inhalation As demonstrated in the Example 7, above, intracoronary delivery of FGF-2 resulted in enhanced FGF-2 deposition compared with i.v. delivery only in myocardial territories subtended by the infused artery. Also, both IC and i.v. delivery strategies resulted in the majority of radiolabed protein being deposited in the liver. Given the presumption that the efficiency of delivery of therapeutic protein via pulmonary administration should be higher than for i.v. delivery, although perhaps not as high as for more direct delivery routes (IC, interpericordial, intermyocardial), the dosage levels developed for IC delivery do not need much adjustment for adaptation to delivery by oral inhalation. In addition, the ease of administration and the non-invasive nature of oral inhalation therapy permit the facile administration of repeated doses should initial dosing prove relatively ineffective. Thus, dosage levels for administration of FGF, VEGF and/or related growth factor proteins can be initiated at levels substantially the same as those utilized for IC delivery. If ineffective, as measured by CPK-MB levels, then either repeated doses, or higher dose loading can be utilized.

Of note, IC delivery resulted in enhanced bFGF deposition compared with i.v. delivery only in myocardial territories subtended by the infused artery. Therefore, for IC delivery to provide an advantage over i.v. delivery, infusion should be carried out in all coronary arteries and bypass grafts if present. Whether infusing a larger dose of bFGF would result in similar myocardial deposition to IC delivery (a more invasive approach) was not investigated. For IC delivery, bFGF was identified on the endothelial cells of the infused arteries, where it might exert its effect. In addition, this study raises an important question of whether more local or sustained delivery is necessary for bFGF effect, particularly with the relatively low cardiac deposition for both delivery modalities.

Example 8

Administration of FGF, VEGF and Related Growth Factor Proteins by Oral Inhalation As demonstrated in the Example 7, above, intracoronary delivery of FGF-2 resulted in enhanced FGF-2 deposition compared with i.v. delivery only in myocardial territories subtended by the infused artery. Also, both IC and i.v. delivery strategies resulted in the majority of radiolabled protein being deposited in the liver. Given the presumption that the efficiency of delivery of therapeutic protein via pulmonary administration should be higher than for i.v. delivery, although perhaps not as high as for more direct delivery routes (IC, interpericordial, intermyocardial), the dosage levels developed for IC delivery do not need much adjustment for adaptation to delivery by oral inhalation. In addition, the ease of administration and the non-invasive nature of oral inhalation therapy permit the facile administration of repeated doses should initial dosing prove relatively ineffective. Thus, dosage levels for administration of FGF, VEGF and/or related growth factor proteins can be initiated at levels substantially the same as those utilized for IC delivery. If ineffective, as measured by CPK-MB levels, then either repeated doses, or higher dose loading can be utilized.

As discussed above, the preferred method of oral inhalation delivery utilizes a dry powder inhalant formulation due to the relative high stability of proteins in the dried crystal form. However, as would be recognized by one of skill in the appropriate art, it is possible to formulate the growth factor proteins in a solution for delivery through oral inhalation of aerosol sprays using existing technology as developed for other therapeutic proteins. See discussion of oral delivery of insulin, and patents referenced therein, above. In particular, in comparison to therapeutic species such as insulin, the delivery parameters for FGF and similar proteins are much less stringent in that the severe, potentially fatal, consequences of administering overdoses of insulin are not of concern. Possible adverse consequences of administration are easily monitored on the clinical level and appropriate adjustments of dose level and dosing frequency can be made.

Accordingly, using technology and skills readily available to one of ordinary skill in the pharmaceutical formulation arts, it is possible to formulate a composition comprising FGF, VEGF and/or related proteins suitable for delivery by oral inhalation, preferably in a dry powder form. Acceptable levels of dosing and a suitable dosing regimen are summarized below:

| Protein | Dose range (adult) | Dosing Schedule |
|---|---|---|
| FGF (acidic or basic) | 10 µg–20 mg | 2 inhalations; repeat at five minutes; twice daily; maintain for seven days |
| VEGF | 10 µg–10 mg | 2 inhalations; repeat at five minutes; twice daily; maintain for seven days |

For acute conditions (MI, angina attack, unstable angina), two sets of double inhalations, five minutes apart should be attempted. Repeat, if necessary, only after assay of CPK-MB levels. Upon confirmation of improvement in CPK-MB levels, remainder of seven-day initial dosing regimen can be resumed. Repeated administration should be discontinued if bronchial spasms occur, or a decline in respiratory function is detected.

Although the above is a complete description of the preferred embodiments of the invention, various alternatives, modifications, and equivalents may be used, as recognized by one of ordinary skill in the appropriate art, based upon the teachings disclosed herein. Therefore, the above description should not be taken as limiting the scope of the invention that is defined by the claims below.

What is claimed is:

1. A method for the administration of a therapeutic amount of a growth factor protein formulation in the treatment of a patient displaying symptoms of acute coronary artery disease comprising the steps of:
   a) administering by inhalation thereby at least one dose of an effective amount of a first therapeutic growth factor protein formulation comprising:
      1. a growth factor protein selected from the group consisting of FGF-1 and FGF-2, and mixtures thereof, and
      2. PlGF;
   b) monitoring one or more clinical indicators of acute coronary artery disease;
   c) determining, based on monitoring the one or more clinical indicators of coronary artery disease, whether an additional dose of a therapeutic growth factor protein formulation is indicated;
   d) depending on the results of step c), administering one or more additional doses of a second growth factor protein formulation comprising:
      1. a growth factor protein being selected from the group consisting of FGF-1 and FGF-2, and mixtures thereof, and
      2. PlGF; and
   e) repeating steps b) through d) until there is a clinical indication of amelioration of the symptoms of acute coronary artery disease in the patient, or until there is a contraindication to continued treatment.

2. The method of claim 1 wherein the growth factor protein formulation is a dry powder formulation.

3. The method of claim 1 wherein the growth factor protein formulation is a liquid aerosol formulation.

4. The method of claim 1, wherein the symptoms of acute coronary artery disease are brought on by reperfusion injury.

5. The method of claim 4, wherein the reperfusion injury is induced by a procedure selected from the group consisting of thrombolytic therapy, bypass surgery and angioplasty.

6. A method for the administration of a therapeutic amount of a growth factor protein formulation in the treatment of a patient displaying symptoms of chronic coronary artery disease comprising the steps of:
   a) administering by inhalation therapy at least one dose of an effective amount of a first therapeutic growth factor protein formulation comprising:
      1. a growth factor protein selected from the group consisting of FGF-1 and FGF-2, and mixtures thereof, and
      2. PlGF;
   b) monitoring one or more clinical indicators of chronic coronary artery disease;
   c) determining, based on monitoring the one or more clinical indicators of chronic coronary artery disease, whether an additional dose of a therapeutic growth factor protein formulation is indicated;
   d) depending on the results of step c), administering one or more additional doses of a second growth factor protein formulation comprising:
      1. a growth factor protein being selected from the group consisting of FGF1 and FGF-2, and mixtures thereof, and
      2. PlGF; and
   e) repeating steps b) through d) until there is a clinical indication of amelioration of the symptoms of chronic coronary artery disease in the patient, or until there is a contraindication to continued treatment.

7. The method of claim 6 wherein the growth factor protein formulation is a dry powder formulation.

8. The method of claim 6 wherein the growth factor protein formulation is a liquid aerosol formulation.

* * * * *